(12) United States Patent
Oku et al.

(10) Patent No.: US 8,642,575 B2
(45) Date of Patent: Feb. 4, 2014

(54) METHOD OF INHIBITING FORMATION OF VOLATILE ALDEHYDES AND/OR DECOMPOSITION OF FATTY ACIDS AND USE THEREOF

(75) Inventors: Kazuyuki Oku, Okayama (JP); Michio Kubota, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 3 days.

(21) Appl. No.: 10/545,078

(22) PCT Filed: Feb. 10, 2004

(86) PCT No.: PCT/JP2004/001409
§ 371 (c)(1),
(2), (4) Date: Aug. 9, 2005

(87) PCT Pub. No.: WO2004/072216
PCT Pub. Date: Aug. 26, 2004

(65) Prior Publication Data
US 2006/0148757 A1 Jul. 6, 2006

(30) Foreign Application Priority Data
Feb. 13, 2003 (JP) .................................. 2003-34882

(51) Int. Cl.
*A01N 43/04* (2006.01)
*A61K 31/715* (2006.01)

(52) U.S. Cl.
USPC .......................................................... 514/61

(58) Field of Classification Search
None
See application file for complete search history.

(56) References Cited

U.S. PATENT DOCUMENTS

| | | | |
|---|---|---|---|
| 5,912,330 A | 6/1999 | Tabuchi et al. | |
| 5,922,691 A | 7/1999 | Mandai et al. | |
| 6,017,899 A | 1/2000 | Maruta et al. | |
| 6,268,353 B1 * | 7/2001 | Chaen et al. | 514/53 |

FOREIGN PATENT DOCUMENTS

| | | |
|---|---|---|
| EP | 0 608 753 A2 | 7/1994 |
| EP | 0 670 368 A2 | 9/1995 |
| EP | 0 983 727 A2 | 3/2000 |
| EP | 0 990 704 A2 | 4/2000 |
| EP | 1 588 627 A1 | 10/2005 |
| JP | 63-240784 | 10/1988 |
| JP | 09-056342 | 3/1997 |

OTHER PUBLICATIONS

Docosahexaenoic acid (DHA) Content of Meats, http://wholefoodcatalog.info/nutrient/docosahexaenoic_acid(dha)/meats/6/, downloaded from the internet Feb. 27, 2012.*
Yoshida et al. Nutrients 2010, 2, 49-59.*
Kingsley et al. Journal of Food Science, vol. 43 (1978), pp. 479-482.*
SkipThePie.org, nutritional information for boiled adzuki beans, downloaded from the internet on Jun. 4, 2013.*
"Method of Analysis in Health Science", 1990, edited by Pharmaceutical Society of Japan, published by Kanehara & Co., Ltd., Tokyo, Japan, 1990, p. 338, lines 4-29 translated.
Excerpt Translation of "Kijun-Yushi-Bunseki-Shiken-Ho" (Standard Method for Analysis of Oils and Fats) Chapters 2.4.12-71 and 2.4.22-73, edited by Japan Oil Chemists' Society. Translation of p. 1 through p. 2, line 5.
T. Hashimoto et al., Inhibitory Action of Maltosyltrehalose on Heat Decomposition of Unsaturated Fatty Acids:, Excerpt translation of A19a05, p. 68,of the summary of lectures in 2003 Annual Meeting in Tokyo by *Japan Society for Bioscience, Biotechnology, and Agrochemistry*.
Ohashi et al., "Innovative crystal transformation of dihydrate trehalose into anhydrogous trehalose using ethanol," Carbohydrate Research 342:819-825 (2007).
Titi Tudorancea Learning Resources, English Edition, entitled "Pork, cured, ham, boneless, extra lean and regular, unheated: Nutrition facts," downloaded on Nov. 25, 2012.
SkipThePie.org: The Nutrition Search Engine, entitled "Nutrition Directory—Legumes and Legume Products," p. 1, which was downloaded on Nov. 27, 2012.
Kimura and Nakakuki, "Maltotetraose, A New Saccharide of Tertiary Property" Starch/Stärke, 42:151-157 (1990).
Wikipedia article on "Sweetness." http://en.wikipedia.org/wiki/Sweetness, downloaded Nov. 30, 2012.
Richter et al, "Sucrose taste thresholds of rats and humans," American Journal of Physiology, 128:291-297 (1940) (Abstract).
ScienceofCooking.com on "taste." http://www.scienceofcooking.com/about_taste.htm, downloaded Nov. 30, 2012.
http://www.hayashibarashoji.jp/product/hello.html, "Halodex", downloaded Jun. 26, 2012.

* cited by examiner

*Primary Examiner* — Layla Bland
(74) *Attorney, Agent, or Firm* — Browdy and Neimark, PLLC

(57) ABSTRACT

The present invention has objects to provide a method for inhibiting the formation of volatile aldehydes and/or the decomposition of fatty acids and use thereof. These objects are attained by establishing a method which comprises incorporating an α-oligoglucosyl α,α-trehalose(s) to a target product to inhibit the formation of volatile aldehydes per se and/or the decomposition of fatty acids per se in fatty acid-containing products; an inhibitory agent for inhibiting the formation of volatile aldehydes and/or the decomposition of fatty acids, which contains an α-oligoglucosyl α,α-trehalose(s) as an effective ingredient; and use thereof to thereby obtain various compositions such as food products, cosmetics, pharmaceuticals, and their materials and intermediates each having a high quality and stability.

1 Claim, No Drawings

METHOD OF INHIBITING FORMATION OF VOLATILE ALDEHYDES AND/OR DECOMPOSITION OF FATTY ACIDS AND USE THEREOF

TECHNICAL FIELD

The present invention relates to a method for inhibiting the formation of volatile aldehydes and/or the decomposition of fatty acids, more particularly, to a method for inhibiting the formation of volatile aldehydes and/or the decomposition of fatty acids which comprises incorporating an α-oligoglucosyl α,α-trehalose(s) into a target product, an agent for inhibiting the formation of volatile aldehydes and/or the decomposition of fatty acids, which contains as an effective ingredient an α-oligoglucosyl α,α-trehalose(s), and use thereof.

BACKGROUND ART

It has been well known that fatty acids with a relatively high purity are substantially free of smell, but they will generate their characteristic unfavorable smell of deteriorated/rancidity smell when irradiated with ultraviolet ray, allowed to stand under atmospheric conditions for a relatively long period of time, or treated by heating. As a method to improve such unfavorable smell, there has been employed from old a method for cooking foods, for example, fatty acid-containing products such as fishery products and meets, with spices such as a capsicum, pepper, wasabi, Japanese pepper, garlic, and ginger. Such a method, however, is not a method for reducing the formation of ingredients of deteriorated/rancidity smell per se, but one for imparting a strong stimulant flavor and taste to the ingredients to mask the unfavorable smell, and as a demerit it may often change preferable flavor and taste, and even color tint inherent to products containing fatty acids. Accordingly, improvement of such a conventional method has been required. In addition to the above fatty acid-containing products, there has been known that, as in the case of rice, denaturation of fatty acids in rice is easily occurred, i.e., rice will promptly reduce in freshness just after milling and may easily generate a smell of rice bran, a kind of deteriorated/rancidity smell. Since the level of such a smell of rice bran is even said to be an index of freshness of rice or a criterion for quality retention, the establishment of a method for inhibiting the smell of rice bran has been strongly desired.

Recently, it has been employed a method for improving smell to inhibit the dispersion of ingredients of deteriorated/rancidity smell, which uses the inclusion action of cyclodextrins. The method, however, has been known to have the defect that the ingredients of deteriorated/rancidity smell, which had been once included by the cyclodextrins, may be replaced with other substances susceptible to the inclusion action and then release the captured unfavorable smell; and that the effect of improving smell is not sufficient.

In view of these conventional defects in conventional prior arts, the present inventors energetically studied the influence of saccharides, i.e., mono- and di-saccharides, on the formation of volatile aldehydes from fatty acids and/or the decomposition of fatty acids, based on a completely novel technical idea of inhibiting the formation of ingredients of deteriorated/rancidity smell, particularly, volatile aldehydes per se and/or the decomposition of fatty acids per se, without improving the formed deteriorated/rancidity smell. As a result, as disclosed in Japanese Patent Kokai No. 2001-123,194, the present inventors had found that α,α-trehalose and/or maltitol significantly inhibit the formation of volatile aldehydes from fatty acids, as well as the decomposition of such fatty acids, and then they provided a method for inhibiting the formation of deteriorated/rancidity smell and compositions, wherein the formation of volatile aldehydes and the decomposition of fatty acids are inhibited by the above method; and they established a novel agent for inhibiting the formation of volatile aldehydes and/or the decomposition of fatty acids and use thereof.

These disaccharides, i.e., α,α-trehalose and maltitol, however, have a lower sweetening power than that of sucrose but have a relatively strong sweetness due to disaccharides. Therefore, when applied to compositions rich in fatty acids, relatively large amounts of α,α-trehalose and maltitol are needed to sufficiently inhibit the formation of volatile aldehydes and/or the decomposition of fatty acids, and this will inevitably over sweeten the resulting compositions and may deteriorate their inherent properties such as taste. Since α,α-trehalose and maltitol are quite easily crystallizable saccharides, they may be crystallized when handled at a relatively high concentration. It was also found that, as the defect, the inhibitory action of the formation of volatile aldehydes and the decomposition of fatty acids as mentioned above will not be expected when α,α-trehalose and maltitol are crystallized.

From these reasons, there has been desired the establishment of oligosaccharides which can inhibit the formation of volatile aldehydes from fatty acids and/or the decomposition of fatty acids and which have a relatively high molecule, lower sweetening power, and non-crystallinity. While, the applicant of the present invention had disclosed in Japanese Patent Kokai No. 143,876/95 that saccharide derivatives of α,α-trehalose are prepared from reducing partial starch hydrolyzates and that the saccharide derivatives can be used in food products, cosmetics, and pharmaceuticals. However, the above-identified Japanese Patent Kokai Nos. 2001-123, 194 and 143,876/95 never disclose anything about whether the saccharide derivatives of α,α-trehalose inhibit the formation of volatile aldehydes and/or the decomposition of fatty acids similarly as in α,α-trehalose and/or maltitol.

DISCLOSURE OF INVENTION

The present invention aims to provide a method for inhibiting the formation of deteriorated/rancidity smell from fatty acids by using a relatively high molecular oligosaccharide; a composition prepared by the method, wherein the formation of volatile aldehydes and/or the decomposition of fatty acids are inhibited; a novel agent for inhibiting the formation of volatile aldehydes and/or the decomposition of fatty acids; and use thereof.

To attain the above objects, the present inventors concentrated on relatively high molecular oligosaccharides including saccharide derivatives of α,α-trehalose and energetically studied them; they studied the influence of oligosaccharides of tetra- or higher-saccharides including derivatives of α,α-trehalose on the effect of inhibiting the formation of volatile aldehydes from fatty acids and the decomposition of fatty acids, when the fatty acids are coexisted with the above oligosaccharides. As a result, the present inventors found that α-oligoglucosyl α,α-trehaloses as saccharide derivatives of α,α-trehaloses, which have a glucose polymerization degree of at least four and which are composed of a maltooligosaccharide and α,α-trehalose bound thereunto via the α-1,4 linkage, showed a significant effect compared with maltooligosaccharides having the same glucose polymerization degrees as α-oligoglucosyl α,α-trehaloses, i.e., α-oligoglucosyl α,α-trehaloses quite remarkably inhibit not only the formation of volatile aldehydes per se but the decomposition of fatty acids. Thus, the present inventors accomplished this invention.

BEST MODE FOR CARRYING OUT THE INVENTION

The first object of the present invention is to provide a method for inhibiting the formation of volatile aldehydes and/or the decomposition of fatty acids, characterized in that it comprises a step of incorporating an α-oligoglucosyl α,α-trehalose(s) into a target product. The second object of the present invention is to provide a composition containing fatty acids, wherein the formation of volatile aldehydes and/or the decomposition of fatty acids are inhibited, by storing fatty acid-containing products in the presence of an α-oligoglucosyl α,α-trehalose(s) and/or processing such products with an α-oligoglucosyl α,α-trehalose(s). The third object of the present invention is to provide an agent for inhibiting the formation of volatile aldehydes and/or the decomposition of fatty acids, which comprises an α-oligoglucosyl α,α-trehalose(s) as an effective ingredient; and to provide use thereof.

The term "α-oligoglucosyl α,α-trehalose(s)" as referred to as in the present invention includes non-reducing saccharides composed of an oligosaccharide having a glucose polymerization degree of at least two, and α,α-trehalose having a glucose polymerization degree of two bound to the oligosaccharide; preferably, saccharides composed of a maltooligosaccharide and α,α-trehalose, which are bound via the α-1,4 linkage. Examples of such are the one with a glucose polymerization degree of four, i.e., α-maltosyl α,α-trehalose; the one with a glucose polymerization degree of five, i.e, α-maltotriosyl α,α-trehalose; the one with a glucose polymerization degree of six, i.e., α-maltotetraosyl α,α-trehalose; and the one with a glucose polymerization degree of seven, i.e, α-maltopentaosyl α,α-trehalose. One or more of these saccharides can be suitably used alone or in combination. Any of these α-oligoglucosyl α,α-trehaloses can be used independently of their origin and properties as long as they can inhibit the formation of volatile aldehydes and/or the decomposition of fatty acids. For example, those in the form of a syrup or crystalline powder, which are preparable by the methods using a non-reducing saccharide forming enzyme disclosed in Japanese Patent Kokai Nos. 143,876/95 and 2000-228,980, can be appropriately used. Examples of mixtures of at least two types of α-oligoglucosyl α,α-trehaloses can be arbitrarily prepared by mixing these saccharides in an appropriate ratio or by allowing a non-reducing saccharide forming enzyme to act on a mixture containing at least two types of maltooligosaccharides with a glucose polymerization degree of four or more, and purifying the formed two or more types of α-oligoglucosyl α,α-trehaloses. The α-oligoglucosyl α,α-trehaloses used in the present invention should not be restricted to highly purified ones and can be arbitrarily used in combination with one or more of the following other saccharides as long as they do not negatively act on the inhibitory effect on the formation of volatile aldehydes and/or the decomposition of fatty acids. Examples of such other saccharides are reducing saccharides such as glucose, maltose, maltotriose, and maltotetraose; non-reducing saccharides such as α,α-trehalose, α-glucosyl α,α-trehalose, sorbitol, maltitol, maltotriitol, maltotetraitol, and a cyclic tetrasaccharide with the structure of cyclo{→6)-α-D-glucopyranosyl-(1→3)-α-D-glucopyranosyl-(1→6)-α-D-glucopyranosyl-(1→3)-α-D-glucopyranosyl-(1→}; cyclodextrins such as α-cyclodextrin, β-cyclodextrin, γ-cyclodextrin, and derivatives thereof; and water-soluble polysaccharides such as gum arabic, pullulan, and elsinan.

Among these α-oligoglucosyl α,α-trehaloses, α-maltotriosyl α,α-trehalose even in the form of a crystal has been known as disclosed in Japanese Patent Kokai No. 2000-228, 980 or 56,342/97. To exert the desired inhibitory effect on the formation of volatile aldehydes and/or the decomposition of fatty acids, the above α-oligoglucosyl α,α-trehaloses, however, should preferably be used in the form of a liquid, syrup, glassy amorphous, or the like.

The term "volatile aldehydes" as referred to as in the present invention means compounds with aldehyde group, which are volatile under ambient temperature conditions. Preferred examples of such are aldehydes with a carbon atom number of 10 or lower; saturated hydrocarbon aldehydes such as methanal (formaldehyde), ethanal (acetaldehyde), propanal, butanal, pentanal, hexanal, octanal, nonanal, and decanal; and unsaturated hydrocarbon aldehydes such as propenal, butenal, pentenal, hexenal, pentanal, octenal, nonenal, heptadienal, and decadienal.

The term "fatty acids" as referred to as in the present invention means fatty acids and salts or esters thereof, which are not substantially volatile under ambient temperature conditions. Preferred examples of fatty acids are higher fatty acids with a carbon atom number of 14 or more; saturated fatty acids such as myristic acid, palmitic acid, stearic acid, arachidic acid, and behenic acid; and unsaturated fatty acids such as myristoleic acid, palmitoleic acid, oleic acid, linoleic acid, linolenic acid, arachidonic acid, eicosapentaenoic acid, and docosahexaenoic acid.

The term "salts of fatty acids" as referred to as in the present invention means salts composed of the above-identified fatty acids and suitable metals such as potassium, sodium, calcium, and magnesium.

The term "esters of fatty acids" as referred to as in the present invention means ester compounds, wherein the carboxyl groups of the above-identified fatty acids are bound to the hydroxyl groups of alcohols, glycerins, or saccharides. Representative examples of such are oils and fats such as triglycerides; phospholipids such as lecithin; and emulsifiers, i.e., surfactants such as monoglycerides, polyglycerides, and sugar esters.

The term "fats and oils" as referred to as in the present invention includes, for example, plant oils such as soybean oil, corn oil, wheat germ oil, rice bran oil, rapeseed oil, mustard oil, sesame oil, peanut oil, saffron oil, cotton seed oil, olive oil, palm oil, and cacao butter; animal oils such as beef tallow, milk fat, lard, chicken fat, egg yolk oil, fish oil, whale oil, liver oil, and bone fat; and hardened oils prepared by hydrogenating the above animal oils. Others are those which are coexisted with fat soluble substances, for example, fat soluble vitamins such as vitamins A, D, E, and K; waxes, terpenoids, steroids, and carotenoids. Of course, lipids contained in lipid membranes for constructing biomembranes and liposomes are included in the lipids as referred to as in the present invention.

The term "fatty acid-containing products" as referred to as in the present invention includes those which contain the above-identified fatty acids or salts or ester derivatives thereof preferably in an amount of at least about 0.1% by weight (throughout the specification, the symbol "% by weight" is abbreviated as "%", unless specified otherwise), more preferably, at least about 0.5%. The fatty acid-containing products can be used independently of their shape, and any of those which are in the form of a liquid, paste, or solid can be used.

Preferred examples of the fatty acid-containing products are those which are in the form of a food product, cosmetic, pharmaceutical, or material/intermediate thereof; or an additive such as an emulsifier.

Examples of such food products and their materials and intermediates include those, which contain the above fatty acids and which are orally or intubationally administrable to humans or domestic animals intact or after further processed, for energy supplementation, maintenance of health, growth promotion, prevention of diseases, and promotion of therapy. Concrete examples of such are agricultural products, for example, fresh fruit; processed fruit and vegetable such as a juice, dried fruit, vegetable extract, powdered vegetable, and pickle; nut and seed pastes such as a sesame paste, peanut paste, and corn paste; "an" (a bean jam) such as a fresh an and strained bean jam; rootstock flours such as a sweet potato flour and Chinese yam; nuts and seeds such as a fresh sesame, brown rice, wheat, barley, rye, soybean, corn, peanut, almond, coffee bean, and cocoa bean, for example, refined cereals such as refined rice, milled rice with embryo, rice without need of washing energy with water before cooking, milled barley, milled Job's teas, and milled common millet; pulverized seeds, for example, pulverized cereals such as a rice flour, wheat flour, barley flour, rye flour, Job's teas flour, soybean flour, flour of soybean with embryo, buckwheat flour, and corn flour; roasted nuts and seeds such as of a sesame, brown rice, wheat, barley, rye, soybean, corn, peanut, almond, coffee bean, and cocoa bean; pulverized nuts and seeds thereof, for example, processed seed products such as a ground sesame, roasted wheat with embryo, powder of roasted grains, powder of roasted soybean, coarse-ground coffee bean; fishery products such as a sardine paste, oyster extract, sea urchin paste, split jack, fish meat, and fish meal; livestock products such as a meat, milk, milk cream, chicken, and egg; seasonings such as a soy sauce, "miso", sauce, mayonnaise, and dressing in the form of a paste or liquid, as well as powdered seasonings such as powdered oils and fats, powdered spices, and "furikake" (a seasoning for cooked rice); Japanese confectionery such as "gyuhi" (a starch paste), sliced and dried rice cake, pop bean, fried bean, fried dough cake, fried rice cracker, and pào de Castella; Western confectionery such as a chocolate, chewing gum, bun, cake, mousse, milk confectionery, cream confectionery, and snack; frozen desserts such as an ice cream and sherbet; teas such as a green tea, roasted tea, black tea, oolong tea, tea with brown rice and green tea, barley water, and Job's tears water; processed rice products such as a cooked rice, steamed rice, rice paste, rice ball, gruel, gelatinized rice, Chinese dish of fried rice, and pilaf; wheat processed products such as a confectionery, bread, pasta, noodle, pizza, nan, bread crumb, and premixed flour; processed products of soybean such as a soybean milk, soybean curd, fried bean curd, bean-curd refuse, hamburg made of bean-curd refuse, and pudding made from soybean milk; fermented food products such as a "koji", "amazake*" (a sweet drink made from fermented rice), sake, "mirin" (a sweet sake), beer, liqueur, vinegar, miso, soy sauce, "nuka-zuke" (a vegetable pickled with bran), "koji-zuke" (a vegetable pickled with koji), "kasu-zuke" (a vegetable pickled in sake lees), "miso-zuke" (a vegetable pickled in miso), and "tamari-zuke" (a vegetable pickled in sauce from refined soy); processed meat products such as a ham and sausage; fish meat paste products such as "kamaboko" (a steamed fish paste), "chikuwa" (a kind of fish paste), and "hanpen" (a fish cake); "chinmi" (relish) such as "uni-no-shiokara" (salted guts of sea urchin), "ika-no-shiokara" (salted guts of squid), dried food products of meat and fish, and others prepared with small fish, shrimp, squid, shellfish, and meat; daily dishes such as "tsukudani" (a food boiled down in soy sauce), "nimame" (cooked beans), salad, pan-fry, fried food, boiled food, egg roll, grilled meat, grilled chicken, hamburg, fried dumpling stuffed with minced pork, "tenpura" (a Japanese deep-fat fried fish paste), "tenkasu" (a fried wheat flour); milk products such as condensed milk, powdered milk, yogurt, butter, cheese, and coffee whitener; processed egg products such as a bavaroise, moose, marshmallow, pudding, cream puff, "kinshi-tamago" (a grilled egg in strips), "dashimaki-tamago" (an egg roll seasoned with a soup stock), pot-steamed hotchpotch, and mayonnaise; bottled and canned products made of meat, fish meat, and chicken; tea beverages made from teas; soft drinks such as a juice of vegetable or fruit, mineral beverage, "amazake" (a sweetened sake), coffee beverage, milk beverage, and lactic acid beverage; alcohols such as sake, wine, and liqueur; instant food products such as an instant wheat vermicelli, instant Chinese noodle, premix of pudding, premix of hot cake, instant soup, retort pouched food, powdered food, and peptide food; feed materials such as a cereal pellet, cereal powder, vegetable oil lees, fermented lees, rice bran, wheat bran, barley bran, defatted bran, defatted soybean, fish meal, fish soluble, powdered meat, powdered blood, powdered feather, skim milk powder, dried whey, chrysalis lees, and $\alpha$-meal; and feed compositions containing the above feed materials. Additives such as sucrose fatty acid esters, glycerine mono-fatty acid esters, and sorbitan fatty acid esters can be exemplified as emulsifiers.

The term "cosmetics" as referred to as in the present invention include those which are in the form of a liquid, paste or solid and which contain the above-identified fatty acids. Examples of such are dentifrices, lip sticks, cachous, gargles, bath salts, deodorants, soaps, shampoos, hair rinses, body soaps, body lotions, deodorant sprays, hair creams, skin-whitening agents, skin-beautifying agents, hair-beautifying agents, and hair restorers.

The term "pharmaceuticals" as referred to as in the present invention include those which are in the form of a liquid, paste, or solid and which contain the above-identified fatty acids. Examples of such are tonics, orally administrable nutrients, intubationally administrable nutrients, fatty acid emulsions for injection, trochees, liver oil drops, ointments, tablets, and capsules.

The term "incorporating" as referred to as in the present invention means a method of contacting/coexisting, and any one of such a step can be used in the present invention as long as it exerts the desired inhibitory effect on the formation of volatile aldehydes from fatty acid-containing products and/or the decomposition of fatty acids, for example, when one or more $\alpha$-oligoglucosyl $\alpha,\alpha$-trehaloses are incorporated into fatty acid-containing products. A preferable method is the one capable of contacting one or more $\alpha$-oligoglucosyl $\alpha,\alpha$-trehaloses with such fatty acid-containing products as homogeneously as possible to incorporate the saccharide(s) into the target/desired products. In the case of the fatty acid-containing products are in a succulent form such as a liquid or paste form, they can be incorporated with one or more $\alpha$-oligoglucosyl $\alpha,\alpha$-trehaloses in the form of a solid such as a powder or crystal, or in the form of a syrup by mixing them as homogeneously as possible.

While in the case that the fatty acid-containing products are in a solid form, one or more $\alpha$-oligoglucosyl $\alpha,\alpha$-trehaloses can be incorporated thereunto in such a manner of allowing the products to make into a juicy condition such as a liquid or paste product using water, and treating the resulting juicy products similarly as above; or allowing one or more $\alpha$-oligoglucosyl $\alpha,\alpha$-trehaloses to make into a syrupy condition, and then spreading, dissolving or suspending the above fatty acid-containing products thereunto as homogeneously as possible. In the case that the fatty acid-containing products are in the form of a water-containing solid or the like, they can be sprayed and mixed with one or more α-oligoglucosyl α,α-trehaloses in the form of a powder or crystal without any further treatment or after pretreatment such as pulverization, and optional dissolution or melting of the α-oligoglucosyl α,α-trehaloses in the products or adhesion, coating, and/or penetration of the saccharides to, over, or into the products. The fatty acid-containing products can be soaked in syrupy products containing one or more α-oligoglucosyl α,α-trehaloses to incorporate the saccharides into the products as homogeneously as possible. While the fatty acid-containing products can be arbitrarily coated with one or more α-oligoglucosyl α,α-trehaloses as homogeneously as possible by spraying aqueous solutions containing such saccharide(s). If necessary, the resulting products can be dehydrated by vacuum drying, air-drying, or spray-drying; or dehydrated by using anhydrous saccharides; and optionally the α-oligoglucosyl α,α-trehaloses, which have been incorporated into the fatty acid-containing products, can be arbitrarily crystallized. Further, the dried products thus obtained can be powdered by using a pulverizer, etc., and the resulting powders can be arbitrarily used intact or optionally granulated and/or tabletted before use, if necessary.

In the case that the fatty acid-containing products are oils and fats such as triglycerides, lipids such as lecithin, and fatty acid esters such as sugar esters as emulsifiers (surfactants), they can be incorporated with one or more α-oligoglucosyl α,α-trehaloses in the form of a powder, crystal or syrup when treated with processings such as stirring, mixing, heating, pressing, emulsifying, pulverizing and drying, followed by advantageously inhibiting the formation of volatile aldehydes and/or the decomposition of fatty acids.

In the case that the fatty acid-containing products are fishery products, for example, fishes such as a jack, sardine, pacific herring, mackerel, yellowtail, tuna, right-eyed flounder, and olive flounder; fish eggs such as a red caviar, salted Alaska pollack roe, and herring roe; eggs and organs of echinoderms such as sea urchins and sea cucumbers; mollusks such as squids and octopuses; crustaceans such as shrimps and mantis shrimps; shellfishes such as baby clams, fresh water clams, abalones, and neptune whelks; and seaweeds such as wakame seaweeds, tangles, *Hizikia fusiformis*, and amanori, they can be incorporated with one or more α-oligoglucosyl α,α-trehaloses in the form of a powder, crystal or syrup when treated with processings such as drying, soaking, baking, boiling, steaming (smothering), frying, or parchong (roasting), followed by advantageously inhibiting the formation of volatile aldehydes and/or the decomposition of fatty acids. Now explaining about the case of tangles, they can be arbitrarily incorporated with one or more α-oligoglucosyl α,α-trehaloses, and the resulting products can be dried in a usual manner to inhibit the formation of volatile aldehydes and/or the decomposition of fatty acids, as well as to inhibit the formation of deteriorated/rancidity smell. The dried tangles can be further pulverized into a powdered seasoning arbitrarily used as a powdered seasoning, which the formation of volatile aldehydes and/or the decomposition of fatty acids are well inhibited.

In the case that the fatty acid-containing products are nuts and seeds, for example, oil seeds such as a soybean, rapeseed, poppy seed, sesame, and peanut; cereals such as a rice, wheat, barley, rye, Job's teas, common millet, and buckwheat; beans such as a soybean, peanut, broad bean, and common peas; nuts and seeds as favorite foods such as an almond, cashew nut, macadamia nut, coffee bean, and cacao bean; and processed intermediates thereof, they can be arbitrarily incorporated with one or more α-oligoglucosyl α,α-trehaloses, and the resulting products can be processed in such a manner of polishing, milling, oil refining, steaming or roasting to arbitrarily inhibit the formation of volatile aldehydes and/or the decomposition of fatty acids. Referring to the case of rice, one or more α-oligoglucosyl α,α-trehaloses are incorporated into brown rice and stored/preserved in a usual manner, and then milled with a rice milling machine into a high-quality milled rice, which the formation of volatile aldehydes and/or the decomposition of fatty acids, as well as the formation of deteriorated/rancidity smell are well inhibited. While, milled rice prepared in a usual manner can be incorporated with one or more α-oligoglucosyl α,α-trehaloses to prepare a high-quality milled rice, which the formation of volatile aldehydes and/or the decomposition of fatty acids, as well as the formation of deteriorated/rancidity smell are well inhibited. Since the formation of rice bran smell and the freshness reduction of the milled rice thus obtained are well inhibited, it can be arbitrarily used for a rice free of washing before cooking or a gelatinized rice, as well as for a cooked rice, steamed rice, rice paste, rice ball, gruel, Chinese dish of fried rice, and pilaf. Referring to the case of wheat germ, it can be incorporated with one or more α-oligoglucosyl α,α-trehaloses, roasted intact or after granulated with an extruder in a usual manner to prepare a roasted wheat germ product, which the formation of volatile aldehydes and/or the decomposition of fatty acids, as well as the formation of deteriorated/rancidity smell are well inhibited. The product can be arbitrarily used intact as a snack or a health food, as well as an intermediate for processing food products.

In the case that the fatty acid-containing products are the following fruits and vegetables, they can be incorporated with one or more α-oligoglucosyl α,α-trehaloses in the form of a powder, crystal or syrup before, during or after processings such as drying, soaking, baking, boiling, steaming/smothering, and frying, whereby the formation of volatile aldehydes and/or the decomposition of fatty acids are well inhibited: Fruits such as a lemon, citron, sudachi (a kind of citron), shaddock, kumquat, banana, pine apple, mango, kiwifruit (*Actinidia chinensis*), strawberry, hawthorn, blueberry, grape, peach, plum, apple, pea, and Japanese persimmon; root vegetables such as a carrot, east Indian lotus, onion, edible burdock, radish, taro, Chinese yam, sweet potato, and potato; vegetables such as a lettuce, chicory, Chinese cabbage, cabbage, kale, Jew's marrow, Angelica keiskel, spinach, *Brassica campestris* var. rapa, "nozawana" (a kind of saltgreen), garland chrysanthemum, pak-choi, angelica tree, young green tea leaf, and perilla leaf; fruit vegetables such as *Abelmoschus esculentus*, cauliflower, broccoli, egg plant, tomato, cucumber, pumpkin, summer squash, sweet pepper, common peas, kidney bean, and *Glycine max*; and mushrooms such as *Lentinula edodes*, velvet-stemmed agaric, and shimeji mushroom. Referring to fried foods cocked with materials such as banana, apple, pumpkin, carrot, potato, and kidney bean, these materials are cut to pieces with an appropriate size after pealed, if necessary, and then incorporated with one or more α-oligoglucosyl α,α-trehaloses. The resulting products, after optionally branched and/or coated and then freezed or not, can be arbitrarily fried in edible oils and fats under normal or reduced pressure to obtain high-quality fried food products such as snack foods, fried noodles, daily dishes, materials for breads and confectionery, and ingredients for instant foods.

The timing for incorporating one or more α-oligoglucosyl α,α-trehaloses into materials for processing fatty acid-containing products is not specifically restricted, and it can be one or more timings before, during or after the processing of the products, as long as it inhibits the formation of volatile aldehydes and/or the decomposition of fatty acids. When the temperature of the fatty acid-containing products increases during their processings, the above saccharides can be preferably incorporated into the products before or during their processings, or even just after their processings until their product temperatures will not be so lowered.

In the case that the fatty acid-containing products are seeds just after processing, which have a relatively high temperature, for example, roasted sesame, rice, wheat, wheat germ, bean, corn with cracking, cocoa bean, and coffee bean, as well as instant noodles and snack foods just after frying, they can be advantageously subjected to the following processing treatment; they can be sprayed with an appropriate amount of an aqueous solution containing one or more α-oligoglucosyl α,α-trehaloses to incorporate the saccharides, and then the aqueous solution is allowed to evaporate to generate steam for eliminating or removing air from the fatty acid-containing products, and allowed to remove heat of evaporation for promptly lowering the temperature of the fatty acid-containing products, whereby the formation of volatile aldehydes and/or the decomposition of fatty acids will be more effectively inhibited.

The amount of one or more α-oligoglucosyl α,α-trehaloses to be incorporated is not specifically restricted as long as it can exert the desired inhibitory effect of the formation of volatile aldehydes and/or the decomposition of fatty acids. Preferably, these saccharides can be incorporated into fatty acid-containing products in a total amount of at least about 12.5%, and desirably, at least 25%, on dry solid basis, to the weight of fatty acids. In general, these saccharides can be incorporated into the products as homogeneously as possible in a total amount of at least about 0.1%, desirably, at least 0.5% but less than about 98%, and more desirably, at least about 1.0% but less than about 90%, on dry solid basis, to the weight of each of the fatty acid-containing products.

According to the present invention, the formation of volatile aldehydes and/or the decomposition of fatty acids in fatty acid-containing products can be advantageously inhibited by incorporating an agent for inhibiting the formation of volatile aldehydes and/or the decomposition of fatty acids, containing as an effective ingredient(s) one or more α-oligoglucosyl α,α-trehaloses (may be simply abbreviated as "inhibitory agent", hereinafter) into the products. The amount of the above-identified saccharides as effective ingredients of the inhibitory agent is not specifically restricted as long as it can exert the desired inhibitory effect on the formation of volatile aldehydes and/or the decomposition of fatty acids. Preferably, the above saccharide(s) can be incorporated into the inhibitory agent in a total amount of at least about 10%, desirably, at least 20%, and more desirably, at least about 50% to the weight of the agent, on a dry solid basis. The inhibitory agent of the present invention can be consisted of one or more α-oligoglucosyl α,α-trehaloses or optionally it can further contain one or more of other substances such as the aforesaid reducing saccharides, non-reducing saccharides, cyclodextrins, water-soluble polysaccharides, spices, sour agents, taste-imparting agents, alcohols, inorganic salts, emulsifiers, antioxidants, and substances with active-oxygen-eliminating action, ultraviolet-ray absorbing action, or chelating action. The above combination use may augment the inhibitory effect on the formation of volatile aldehydes and/or the decomposition of fatty acids or exert the effect of improving taste or undesirable smell. The inhibitory agent thus obtained may have any form of a syrup, powder, granule, tablet, or the like, and it can be used independently of its use as long as it can exert the desired inhibitory effect on the formation of volatile aldehydes and/or the decomposition of fatty acids. For example, the inhibitory agent can be used in accordance with the method of inhibiting the formation of volatile aldehydes from fatty acid-containing products and/or the decomposition of fatty acids in the products by incorporating these saccharides into the products. Desirably, both of the above inhibition and the preservation stability of the fatty acid-containing products can be attained by incorporating the inhibitory agent into the products and then treating the resulting products with methods similarly as in the aforesaid methods for incorporating one or more α-oligoglucosyl α,α-trehaloses during preservations at ambient temperature or cooled conditions, and/or during cookings such as drying, soaking, baking, boiling, steaming/smothering, frying, and grilling (roasting); or processings such as polishing, milling, oil refining, steaming, and roasting. The combination use of the inhibitory agent and the following products will exert the desired inhibitory effect on the formation of volatile aldehydes from fatty acid-containing products and/or the decomposition of fatty acids in the products and make the products into daily dishes and cooked dishes in pots with satisfactory flavor and taste; seasonings such as a soy sauce, miso, sauce, seasoned sauce for grilled meat, ketchup, mayonnaise, dressing, margarine, butter, cheese, salad oil, Japanese deep frying oil, sesame oil, hot sesame oil, oyster oil, paste of *Wasabia japonica*, paste of mustard, ground ginger, vinegar, "mirin" (a sweet sake), "shin-mirin" (a kind of mirin), sake, wine, liqueur, seasonings of amino acids and/or nucleic acids, and salt. Seasonings containing fatty acids such as mayonnaises and dressings with satisfactory color tint, taste/flavor, and preservation stability can be advantageously produced by incorporating the inhibitory agent of the present invention into their materials during processings.

The combination use of the inhibitory agent of the present invention and fatty acid-containing materials or intermediates for cosmetics or pharmaceuticals advantageously facilitates the production of high-quality and stable cosmetics and pharmaceuticals, which exert the desired inhibitory effect of the formation of volatile aldehydes and/or the decomposition of fatty acids. Particularly, in the case of cosmetics, they have a satisfactory stability in themselves and inhibit the formation of volatile aldehydes and/or the decomposition of fatty acids derived from or present in the sweat, dirt, dandruff, sebum, etc., adhered to the skin of a subject to be applied with the inhibitory agent. Accordingly, such cosmetics will prevent the formation of body odor and the stimulation and itch in the skin, and treat/prevent pigmentation such as stain, freckle, and sunburn.

The following experiments explain the present invention in detail: Experiment 1 explains the preparation of α-oligoglucosyl α,α-trehaloses, and Experiments 2 to 5 explain the influence of the coexistence of α-oligoglucosyl α,α-trehaloses on the formation of volatile aldehydes and/or deteriorated/rancidity smell from fatty acids or products containing them. Experiments 6 to 9 explain the influence of the coexistence of α-oligoglucosyl α,α-trehaloses on the decomposition of fatty acids, and Experiments 10 to 13 explain the influence of the coexistence of α-oligoglucosyl α,α-trehaloses on the deterioration/rancidity of fatty acids.

Experiment 1-1

Preparation of α-maltosyl α,α-trehalose

Maltotetraose with a purity of 97.9%, produced by Hayashibara Biochemical Laboratories, Inc., Okayama, Japan, was dissolved in water to obtain 2,500 g of a 40%

(w/w) aqueous saccharide solution, adjusted to give a pH of 7.0 with 1M aqueous sodium hydroxide solution, and kept at 4° C. before use. To the resulting saccharide solution was added four units/g solid of a non-reducing saccharide-forming enzyme from *Arthrobacter* sp. Q36 strain, prepared in accordance with the method disclosed in Japanese Patent Kokai No. 143,876/95, adjusted to give a pH of 7.0, enzymatically reacted at 40° C. for 38 hours, heated to about 98° C., and incubated at the temperature for 15 min to suspend the enzymatic reaction. The reaction mixture was sampled and analyzed on high-performance liquid chromatography (abbreviated as ""HPLC" hereinafter), revealing that the formed α-maltosyl α,α-trehalose had a purity of about 74.3%. The above reaction mixture was adjusted to give a pH of about 12.5 by dissolving sodium hydroxide granules, heated to about 98° C., and incubated at the temperature for about 90 min while retaining the pH at about 12.5 by gradually adding sodium hydroxide granules and decomposing the remaining reducing sugars by alkaline hydrolysis. After cooling with water, the mixture was in a usual manner desalted with ion exchangers, decolored, and filtered with an activated charcoal, filtered using a membrane with a pore size of 0.45 μm, concentrated by an evaporator, and dried in vacuo to obtain about 779 g of a powder. The powder contained α-maltosyl α,α-trehalose with a purity of about 98.7% and had a moisture content of 7.18%.

HPLC was carried out as follows: The above reaction mixture was fed to two columns of "MCI GEL CK04SS", a column for HPLC, having 10 mm in diameter and 200 mm in length, commercialized by Mitsubishi Chemical Corporation, Tokyo, Japan, which had been cascaded in series, at an inner column temperature of 80° C. and a flow rate of 0.4 ml/min of water as an eluent, and then the reaction products were analyzed on "RI-8020", a differential refractometer commercialized by Toso Corporation, Tokyo, Japan.

Experiment 1-2

Preparation of α-maltotriosyl α,α-trehalose

Maltopentaose with a purity of 98.3%, produced by Hayashibara Biochemical Laboratories, Inc., Okayama, Japan, was dissolved in water to obtain 2,000 g of a 50% (w/w) aqueous saccharide solution, adjusted to give a pH of 7.0 with 1M aqueous sodium hydroxide solution, and kept at 40° C. before use. To the resulting saccharide solution was added one and half units/g solid of a non-reducing saccharide-forming enzyme from *Arthrobacter* sp. Q36 strain, prepared in accordance with the method disclosed in Japanese Patent Kokai No. 143,876/95, adjusted to give a pH of 7.0, enzymatically reacted at 40° C. for 24 hours, cooled to about 8° C., and then kept at the temperature for 24 hours to crystallize the formed α-maltotrioxyl α,α-trehalose. The resulting reaction mixture with crystals was heated to 40° C., subjected to an enzymatic reaction for 24 hours, heated to about 98° C., and then kept at the temperature for 15 min to suspend the enzymatic reaction. The resulting reaction mixture was cooled to ambient temperature and then allowed to stand overnight to crystallize α-maltotriosyl α,α-trehalose, followed by collecting the crystals with a glass filter. The crystals thus obtained were dissolved in water to obtain 6,580 g of a 13% aqueous saccharide solution. HPLC analysis for saccharide composition revealed that the saccharide solution contained α-maltotriosyl α,α-trehalose with a purity of about 92%. Similarly as in Experiment 1-1, the saccharide solution was subjected to alkaline hydrolysis, desalting, decoloring, and filtering. The resulting filtrate was concentrated with an evaporator up to give a total volume of about 1,800 g, and allowed to stand overnight to crystallize α-maltotriosyl α,α-trehalose, followed by collecting the crystals using a basket-type centrifuge. The collected crystals were dried in vacuo to obtain about 700 g of a crystalline powder having α-maltotriosyl α,α-trehalose with a purity of about 99.4% and a water content of 4.94%.

Experiment 1-3

Preparation of α-maltotetraosyl α,α-trehalose

Maltohexaose with a purity of 98.0%, produced by Hayashibara Biochemical Laboratories, Inc., Okayama, Japan, was dissolved in water to obtain 1,000 g of a 40% (w/w) aqueous solution, adjusted to give a pH of 7.0 with 1M aqueous sodium hydroxide solution, and kept at 40° C. before use. Similarly as in Experiment 1-2, to the resulting saccharide solution was added one and half units/g solid of a non-reducing saccharide-forming enzyme, adjusted to give a pH of 7.0, and incubated at 40° C. for 24 hours. Then, similarly as in Experiment 1-1, the enzymatic reaction was suspended, subjected to alkaline treatment, desalted, decolored, filtered, concentrated, and dried in vacuo to obtain about 320 g of a powder having α-maltotetraosyl α,α-trehalose with a purity of about 97.5% and a water content of 5.25%.

Experiment 1-4

Preparation of α-maltopentaosyl α,α-trehalose

Maltoheptaose with a purity of 96.6%, produced by Hayashibara Biochemical Laboratories, Inc., Okayama, Japan, was dissolved in water to obtain 1,000 g of a 40% (w/w) aqueous saccharide solution, adjusted to give a pH of 7.0 with 1M aqueous sodium hydroxide solution, and kept at 40° C. before use. Similarly as in Experiment 1-2, to the resulting saccharide solution was added one and half units/g solid of a non-reducing saccharide-forming enzyme, adjusted to give a pH of 7.0, and incubated at 40° C. for 24 hours. Then, similarly as in Experiment 1-1, the enzymatic reaction was suspended, subjected to alkaline treatment, desalted, decolored, filtered, concentrated, and dried in vacuo to obtain about 305 g of a powder having α-maltopentaosyl α,α-trehalose with a purity of about 96.2% and a water content of 5.87%.

Experiment 2-1

Influence of the Coexistence of α-oligoglucosyl α,α-trehaloses and Maltooligosaccharides on the Formation of Volatile Aldehydes and/or Deteriorated/Rancidity Smell from α-linolenic Acid when Heated One hundred milligrams of α-linolenic acid, 0.5 g of a cellulose powder, and 0.25 ml of 0.6M-phosphate buffer (pH 6.0) were placed in a 20-ml vial. To the vial one milliliter of a 5% (w/v) aqueous solution containing as a saccharide 50 mg, d.s.b., of any one of α-maltosyl α,α-trehalose, α-maltotriosyl α,α-trehalose, α-maltotetraosyl α,α-trehalose, and α-maltopentaosyl α,α-trehalose, which had been prepared by the method in Experiments 1 to 4; and other saccharides which had been used as materials for preparing the above α-oligoglucosyl α,α-trehaloses such as maltotetraose, maltopentaose, maltohexaose, and maltoheptaose, which were all produced by Hayashibara Biochemical Laboratories, Inc., Okayama, Japan. Thus, eight vials as test samples differing from each other in terms of added saccharide were prepared, and as a control a vial free of saccharide, only differing from the test samples in terms of the presence/absence of saccharide, was prepared. All of these vials were sealed with butyl rubber bungs and subjected to 1-hour heat treatment at 100° C. Thereafter, the vials were cooled to ambient temperature and heated for five minutes in an aluminum block preheated at 80° C., followed by sampling two milliliters of a head space gas (hereinafter abbreviated as "HSG") from each vial with a gas syringe and subjecting the sampled HSG to gas chromatography (hereinafter abbreviated as "GLC") for analysis of volatile aldehydes using the following apparatuses and conditions: "GC-14B", an apparatus for GLC commercialized by Shimadzu Corporation, Tokyo, Japan; "TC-FFAP", a capillary column for analysis, 0.53 mm in diameter, 30 m in length, and 1.0 μm thickness, commercialized by GL Sciences Inc., Tokyo, Japan; helium gas as a carrier gas was used at a flow rate of 10 ml/min; 200° C. as an injection temperature; as the conditions of column oven temperature after keeping at 40° C. for five minutes, it was heated up to 230° C. at a rate of 5° C./min; and a hydrogen flame ionization detector was used as a detector. Six veteran panels conducted a sensory test for deteriorated/rancidity smell of test and control samples in such a manner that they directly smelled them. In this test, the results were evaluated based on the number of panels who answered the samples with saccharides had substantially the same, stronger, or lesser deteriorated/rancidity smell compared with the control sample with no saccharide.

The analytical data on HSG and the evaluation results from the sensory test are tabulated in Table 1.

TABLE 1

| Saccharide | Concentration of volatile aldehydes in HSG from α-linolenic acid (μg/ml) | | | Sensory evaluation on deteriorated/rancidity smell |
|---|---|---|---|---|
| | Propanal | Butanal | Hexanal | |
| None | 13.91 | 0.24 | 0.11 | +++ |
| α-Maltosyl α,α-trehalose | 3.25 | 0.02 | 0.02 | + |
| α-Maltotriosyl α,α-trehalose | 3.30 | 0.02 | 0.01 | + |
| α-Maltotetraosyl α,α-trehalose | 4.02 | 0.04 | 0.02 | + |
| α-Maltopentaosyl α,α-trehalose | 4.25 | 0.05 | 0.03 | + |
| Maltotetraose | 12.88 | 0.24 | 0.10 | +++ |
| Maltopentaose | 13.58 | 0.25 | 0.11 | +++ |
| Maltohexaose | 13.99 | 0.20 | 0.12 | +++ |
| Maltoheptaose | 13.42 | 0.23 | 0.10 | +++ |

In the table, the symbol "+++" represents that the number of panels, who answered the test samples coexisted with saccharides had substantially the same and a stronger deteriorated/rancidity smell compared with the control sample coexisted with no saccharide, was at least four among six panels;
the symbol "+" represents that the number of panels, who answered the test samples coexisted with saccharides had a lesser deteriorated/rancidity smell than that of the control sample coexisted with no saccharide, was at least four among six panels; and
the symbol "++" represents a rank between the above two evaluations.

In the table, the symbol "+++" represents that the number of panels, who answered the test samples coexisted with saccharides had substantially the same or a stronger deteriorated/rancidity smell than that of the control sample with no saccharide, was at least four among the six panels; the symbol "+" represents that the number of panels, who answered the test samples coexisted with saccharides had a lesser deteriorated smell than that of the control sample with no saccharide, was at least four among the six panels; and the symbol ++ represents a rank between the above two evaluations. As evident from the results in Table 1, it was revealed that, as compared with the control system with no saccharide, the test systems coexisted with α-oligoglucosyl α,α-trehaloses such as α-maltosyl α,α-trehalose, α-maltotriosyl α,α-trehalose, α-maltotetraosyl α,α-trehalose, and α-maltopentaosyl α,α-trehalose showed a significantly lower concentration of propanal, butanal, and hexanal in HSG formed by heat decomposition of α-linolenic acid; and a significantly lesser deteriorated/rancidity smell based on the sensory evaluation. On the sensory evaluation, the systems coexisted with any one of maltotetraose, maltopentaose, maltohexaose, and maltoheptaose showed no difference compared with the control system coexisted with no saccharide, though some of the systems gave a rather lower concentration of volatile aldehydes in HSG than that of the control system.

Experiment 2-2

Influence of the Coexistence of α-oligoglucosyl α,α-trehaloses and Maltooligosaccharides on the Formation of Volatile Aldehydes and/or Deteriorated/Rancidity Smell from Linoleic Acid Except for using 100 mg of linoleic acid as a fatty acid, the fatty acid was subjected to heat treatment similarly as in Experiment 2-1 and analyzed for the formed volatile aldehydes in HSG. The deteriorated/rancidity smell was subjected to a sensory evaluation similarly as in Experiment 2-1.

The analytical data on HSG and the evaluation results from the sensory test are tabulated in Table 2.

TABLE 2

| Saccharide | Concentration of volatile aldehydes from linoleic acid in HSG (μg/ml) | | | | Sensory evaluation on deteriorated/rancidity smell |
|---|---|---|---|---|---|
| | Propanal | Butanal | Hexanal | 2,4-Decadienal | |
| Non | 10.77 | 0.78 | 0.11 | 10.01 | +++ |
| α-Maltosyl α,α-trehalose | 3.12 | 0.24 | 0.04 | 3.30 | + |
| α-Maltotriosyl α,α-trehalose | 3.45 | 0.25 | 0.04 | 3.57 | + |
| α-Maltotetraosyl α,α-trehalose | 4.01 | 0.27 | 0.03 | 3.99 | + |

TABLE 2-continued

| Saccharide | Concentration of volatile aldehydes from linoleic acid in HSG (μg/ml) | | | | Sensory evaluation on deteriorated/rancidity smell |
|---|---|---|---|---|---|
| | Propanal | Butanal | Hexanal | 2,4-Decadienal | |
| α-Maltopentaosyl α,α-trehalose | 4.52 | 0.30 | 0.05 | 4.75 | + |
| Maltotetraose | 10.02 | 0.74 | 0.10 | 10.21 | +++ |
| Maltopentaose | 10.88 | 0.79 | 0.12 | 10.01 | +++ |
| Maltohexaose | 11.02 | 0.75 | 0.12 | 11.00 | +++ |
| Maltoheptaose | 10.55 | 0.80 | 0.10 | 10.58 | +++ |

In the table, the symbol "+++" represents that the number of panels, who answered the test samples coexisted with saccharides had substantially the same or a stronger deteriorated/rancidity smell than that of the control sample with no saccharide, was at least four among the six panels;
the symbol "+" represents that the number of panels, who answered the test samples coexisted with saccharides had a lesser deteriorated/rancidity smell than that of the control sample with no saccharide, was at least four among the six panels; and
the symbol "++" represents a rank between the above two evaluations.

As evident from the results in Table 2, the systems coexisted with α-oligoglucosyl α,α-trehaloses such as α-maltosyl α,α-trehalose, α-maltotriosyl α,α-trehalose, α-maltotetraosyl α,α-trehalose, and α-maltopentaosyl α,α-trehalose showed a significantly lower concentration of propanal, butanal, hexanal, and 2,4-decadienal in HSG formed by heat decomposition of α-linoleic acid; and a significantly lesser deteriorated/rancidity smell based on the sensory evaluation. Upon the sensory evaluation, the systems coexisted with maltotetraose, maltopentaose, maltohexaose, and maltoheptaose showed substantially the same level of concentration of volatile aldehydes in HSG as that of the control system with no saccharide, and gave no significant difference between the test systems and the control system.

Experiment 2-3

Influence of α-maltosyl α,α-trehalose on the Formation of Volatile Aldehydes from Linoleic Acid when Heated Except for using 100 mg of linoleic acid as a fatty acid and one milliliter of a 0 to 5% (w/v) aqueous α-maltosyl α,α-trehalose solution containing as a saccharide 0, 12.5, 25, 50 or 100 mg of α-maltosyl α,α-trehalose, test vials were prepared by the method similarly as in Experiment 2-1, and then subjected to heat treatment and analysis of volatile aldehydes in HSG.

The analytical data on HSG are tabulated in Table 3.

TABLE 3

| Saccharide | Saccharide added (mg) | Percentage of saccharide to fatty acid (%) | Concentration of volatile aldehydes from linoleic acid in HSG (μg/ml) | | | | |
|---|---|---|---|---|---|---|---|
| | | | Propanal | Butanal | Hexanal | 2,4-Decadienal | Total |
| α-Maltosyl α,α-trehalose | 0.0 | 0.0 | 10.77 | 0.78 | 0.11 | 10.01 | 21.67 |
| | 12.5 | 12.5 | 7.98 | 0.61 | 0.07 | 8.02 | 16.68 |
| | 25.0 | 25.0 | 5.87 | 0.47 | 0.05 | 6.25 | 12.64 |
| | 50.0 | 50.0 | 3.12 | 0.24 | 0.04 | 3.30 | 6.70 |
| | 100.0 | 100.0 | 0.95 | 0.10 | 0.02 | 0.94 | 2.01 |

As evident from the results in Table 3, the systems coexisted with α-maltosyl α,α-trehalose gave lower concentrations of propanal, butanal, hexanal, and 2,4-decadienal, which were formed by heat decomposition of linoleic acid an detected in HSG, than those of the control system with no saccharide. The concentrations of volatile aldehydes in HSG of the test systems were lowered as the increase of the saccharide added, i.e., the total amount of volatile aldehydes was lowered to about 58% with respect to that of the control system with no saccharide when the saccharide was added in an amount of 25 mg, corresponding to the added amount of 25%, d.s.b., of α-maltosyl α,α-trehalose to linoleic acid as a fatty acid. Similarly, it was revealed the addition of the saccharide in an amount of at least 50% or 100% to the fatty acid lowered the total amount of volatile aldehydes to about 31% and about 9% with respect to the control system with no saccharide.

Experiment 3

Influence of the Coexistence of Saccharides on the Dispersion of Standard Volatile Aldehydes The following experiment was conducted to confirm the fact that whether the reduction of volatile aldehydes in HSG of the test systems coexisted with α-oligoglucosyl α,α-trehaloses in Experiments 2-1 and 2-3 was induced by the inhibition of the formation of volatile aldehydes from α-linolenic acid or linoleic acid or by the inhibition of the dispersion of the formed volatile aldehydes. Using standard propanal, butanal, hexanal and 2,4-decadienal as volatile aldehydes, it was examined the influence of coexisted α-maltosyl α,α-trehalose, α-maltotriosyl α,α-trehalose, maltotetraose or maltopentaose on the dispersion of the above volatile aldehydes: Ten milligrams of propanal, butanal, hexanal, or 2,4-decadienal, 0.5 g of a cellulose powder, 0.25 ml of 0.6M-phosphate buffer (pH 6.0), and one milliliter of a 5% (w/v) aqueous solution containing 50 mg, d.s.b., of any one of the above saccharides were placed in a 20-ml vial which was then sealed with a butyl rubber bung and heated for five minutes in an aluminum block preheated at 80° C., followed by sampling two milliliters of HSG from each vial with a gas syringe and subjecting the sampled HSG to GLC for analysis of volatile aldehydes. Similarly as above, a control system free of any saccharide was prepared.

The dispersion concentration (μg/ml) of each of the standard aldehydes into HSG was detected and expressed with a relative value with respect to the value of the control system being regarded as 100. The results are in Table 4.

TABLE 4

| | Dispersion of standard volatile aldehydes into HSG | | | |
|---|---|---|---|---|
| Saccharide | (μg/ml) | Relative concentration | (μg/ml) | Relative concentration |
| | Propanal | | Butanal | |
| None | 10.23 | 100 | 9.03 | 100 |
| α-Maltosyl α,α-trehalose | 10.54 | 103 | 8.33 | 92 |
| α-Maltotriosyl α,α-trehalose | 10.20 | 100 | 8.98 | 99 |
| Maltotetraose | 11.34 | 111 | 8.55 | 95 |
| Maltopentaose | 10.78 | 105 | 9.25 | 102 |
| | Hexanal | | 2,4-Decadienal | |
| None | 7.22 | 100 | 5.77 | 100 |
| α-Maltosyl α,α-trehalose | 7.01 | 97 | 5.63 | 98 |
| α-Maltotriosyl α,α-trehalose | 7.25 | 100 | 5.69 | 99 |
| Maltotetraose | 7.33 | 102 | 5.75 | 100 |
| Maltopentaose | 7.13 | 99 | 5.78 | 100 |

As evident from the results in Table 4, the systems coexisted with α-maltosyl α,α-trehalose or α-maltotriosyl α,α-trehalose as an α-oligoglucosyl α,α-trehalose gave substantially the same levels of relative concentrations of standard propanal, butanal, hexanal and 2,4-decadienal in HSG as those of the control systems free of any saccharide or with maltotetraose or maltopentaose as a maltooligosaccharide. The data revealed that the coexistence of α-oligoglucosyl α,α-trehaloses could not inhibit the dispersion of propanal, butanal, hexanal, and 2,4-decadienal into HSG and did not influence on their dispersion. Thus, it can be concluded that the inhibitory action of deteriorated/rancidity smell, exerted by the coexistence of α-oligoglucosyl α,α-trehaloses as shown in Tables 1 to 3, was not induced by the inhibition of the dispersion of volatile aldehydes by these saccharides but the inhibition of the formation of volatile aldehydes from unsaturated fatty acids when α-linolenic acid and linoleic acid were heated.

Experiment 4-1

Influence of the coexistence of α-oligoglucoyl α,α-trehaloses and maltooligosaccharides on the Formation of Volatile Aldehydes from Products Containing Plant Fatty Acids A rice, produced from Okayama prefecture, Japan, in 2002, was used as a product containing plant fatty acids. Two hundred grams of a milled rice with a temperature of about 40° C. just after milling the above rice were placed in a 500-ml polyethylene bag, 0.115 mm in thickness, admixed with four grams of either an α-maltosyl α,α-trehalose fine powder, as an α-oligoglucosyl α,α-trehalose, prepared by the method in Experiment 1-1, or a maltotetraose fine powder, as a maltooligosaccharide, produced by Hayashibara Biochemical Laboratories, Inc., Okayama, Japan, as homogeneous as possible; sealed; cooled by placing in a thermostat controlled at 25° C.; and stored at the temperature. After two-weeks of storing, five grams of the milled rice were sampled from each of the polyethylene bags and placed in a 20-ml vial, sealed with a butyl rubber bung, and heated for five minutes in an aluminum block preheated at 60° C., followed by sampling one milliliter of HSG from each vial with a gas syringe and subjecting the sampled HSG to GLC analysis of volatile aldehydes to examine the contents of volatile aldehydes formed from one gram of the milled rice after two-weeks of storing, similarly as in Experiment 2-1. As a control, a control system was provided similarly as above except for omitting the addition of any saccharide, and treated similarly as above.

The results are tabulated in Table 5.

TABLE 5

| | Amount of volatile aldehydes in HSG (μg/g milled rice) | | | | |
|---|---|---|---|---|---|
| Saccharide | Propanal | Butanal | Pentanal | Hexanal | Total |
| None | 1,250 | 376 | 7.4 | 0.34 | 1,634 |
| α-Maltosyl α,α-trehalose | 428 | 80 | 4.1 | 0.00 | 512 |
| Maltotetraose | 765 | 105 | 5.3 | 0.11 | 875 |

As evident from the results in Table 5, after two-weeks of storing, the test system coexisted with α-maltosyl α,α-trehalose showed a significantly lower formation level of volatile aldehydes in HSG than those of the control system with no saccharide, revealing that the coexistence of α-maltosyl α,α-trehalose as an α-oligoglucosyl α,α-trehalose in storing milled rice significantly inhibits the formation of volatile aldehydes from the milled rice. Particularly, no formation of hexanal as a main ingredient of smell of rice bran or long-stored rice. While the inhibitory level of maltotetraose as a maltooligosaccharide was considerably lower than that of α-maltosyl α,α-trehalose as an α-oligoglucosyl α,α-trehalose. Accordingly, the results in this Experiment 4-1 indicate that the coexistence of an α-oligoglucosyl α,α-trehalose in milled rice inhibits the lowering of freshness of milled rice and well maintains its original freshness.

Experiment 4-2

Influence of α-maltosyl α,α-trehalose on the Formation of Ingredients of Deteriorated/Rancidity Smell from Products Containing Plant Fatty Acids A brown rice was used as a product containing plant fatty acids. Five hundred grams of a brown rice, produced from Okayama prefecture, Japan, in 2002, were placed in a 500-ml polyethylene bag with a thickness of 0.115 mm, admixed with 10 g of an α-maltosyl α,α-trehalose fine powder prepared by the method in Experiment 1-1 to homogeneously adhere the saccharide to the brown rice. Twenty grams aliquots of the mixture were respectively placed in three 50-ml vials, sealed with butyl rubber bungs, and stored in a thermostat controlled at 50° C. On day 0, 7 and 14 after initiating the storing, one milliliter of HSG was sampled once from either of the three vials with a gas syringe, followed by analyzing the main volatile ingredients of deteriorated/rancidity smell in the samples on GLC similarly as in Experiment 2-1. As a control, a system was provided similarly as above except for omitting the addition of α-maltosyl α,α-trehalose, and treated similarly as above. The amount of the main ingredients newly formed from one gram of the brown rice was determined on day 0, 7 and 14 after initiation of storing. The results are tabulated in Table 6.

TABLE 6

| Storage period (day) | Coexistence of α-maltosyl α,α-trehalose | Amount of volatile aldehydes in HSG (μg/g brown rice) | | | | |
|---|---|---|---|---|---|---|
| | | Ethyl acetate | Ethanol | Ethanal | Propanal | Hexanal | Total |
| 0 | No | 0.00 | 92.5 | 0.00 | 31.8 | 0.00 | 124.3 |
| | Yes | 0.00 | 75.0 | 0.00 | 28.7 | 0.00 | 103.7 |
| 7 | No | 1.45 | 134.3 | 4.15 | 55.7 | 0.00 | 195.6 |
| | Yes | 0.00 | 97.1 | 2.20 | 29.8 | 0.00 | 127.1 |
| 14 | No | 2.87 | 230.9 | 7.56 | 116.3 | 2.36 | 360.0 |
| | Yes | 0.00 | 168.5 | 3.38 | 90.2 | 0.00 | 262.1 |

As evident from the results in Table 6, the system coexisted with α-maltosyl α,α-trehalose in storing brown rice gave a lower formation level of the ingredients containing volatile aldehydes of deteriorated/rancidity smell than that of the control system with no such saccharide. This revealed that the coexistence of α-maltosyl α,α-trehalose well inhibits the formation of the ingredients of deteriorated/rancidity smell per se.

Experiment 5

Influence of the Coexistence of Saccharides on the Formation of Volatile Aldehydes from Products Containing Animal Fatty Acids A mackerel meat was used as a product containing animal fatty acids. The meat was minced with a mincer, and 10 g of which were placed in a 50-ml vial, admixed with five milliliters of an aqueous solution containing 0.5, 1 or 2 g of α-maltosyl α,α-trehalose, corresponding to an amount of 5, 10 or 20% to the weight of the meat, sealed with a butyl rubber bung, and heated for 15 min in a boiling water bath. Thereafter, the vials were cooled to ambient temperature, heated for five minutes in an aluminum block preheated at 80° C., followed by sampling one milliliter of HSG from each vial with a gas syringe and subjecting the sampled HSG for analysis of volatile aldehydes, trimethylamine, and ethyl mercaptan. Volatile aldehydes and trimethylamine other than methanal were analyzed on GLC. Methanal and ethyl mercaptan were respectively analyzed using "GASTECH No. 91L and No. 72L", gas detecting tubes commercialized by GL Sciences Inc., Tokyo, Japan, in such a manner of sampling five milliliters of HSG from each of the vials, which had been treated similarly as above, with a gas syringe and allowing the total gas to pass through the tubes to determine the concentrations of methanal and ethyl mercaptan. As controls, a system with no saccharide and another system, coexisted with sorbitol as a comparative saccharide in an amount of 10% or 20% to the weight of the mackerel meat, were provided.

The volatile aldehydes formed from one gram of mackerel meat were quantified and the results are tabulated in Table 7, while the amounts of trimethylamine and ethyl mercaptan were similarly determined and the results are tabulated in Table 8.

TABLE 7

| Saccharide | Amount of volatile aldehydes in HSG (ng/g mackerel meat) | | | | |
|---|---|---|---|---|---|
| | Methanal | Ethanal | Propanal | Hexanal | Heptanal |
| None | 743 | 698 | 190 | 61.3 | 11.2 |
| α-Maltosyl α,α-trehalose | | | | | |
| 5% | 231 | 205 | 87 | 15.7 | 3.3 |
| 10% | 153 | 124 | 40 | 9.1 | 1.9 |
| 20% | 91 | 85 | 27 | 7.2 | 1.8 |
| Sorbitol | | | | | |
| 10% | 462 | 383 | 128 | 27.6 | 6.5 |
| 20% | 283 | 156 | 100 | 21.3 | 4 |

TABLE 8

| Saccharide | Amount of ingredients of volatile aldehydes in HSG (ng/g mackerel meat) | |
|---|---|---|
| | Trimethylamine | Ethyl mercaptan |
| None | 9.02 | 115 |
| α-Maltosyl α,α-trehalose | | |
| 5% | 4.51 | 53 |
| 10% | 2.40 | 42 |
| 20% | 1.67 | 31 |
| Sorbitol | | |
| 10% | 7.71 | 113 |
| 20% | 5.76 | 86 |

As evident from the results in Table 7, it was revealed that the systems coexisted with α-maltosyl α,α-trehalose gave a significantly lower formation level of every volatile aldehyde in HSG than those of the control system with no saccharide and another control system coexisted with sorbitol conventionally well used in fishery products such as sausages and fish meat pastes. It was also revealed that the coexistence of α-maltosyl α,α-trehalose significantly inhibited the formation of volatile aldehydes when fish meat is heated, and the effect will positively increase as the increase of the amount of α-maltosyl α,α-trehalose added. As evident from the results in Table 8, the existence of α-maltosyl α,α-trehalose significantly inhibits the formation of trimethylamine and ethyl mercaptan as a characteristic smell of fishery products, and the effect positively increases as the increase of α-maltosyl α,α-trehalose added.

Experiment 6

Influence of the Coexistence of Saccharide on the Decomposition of Linoleic Acid when Irradiated One hundred milligrams of linoleic acid, 0.5 g of a cellulose powder, 0.25 ml of 0.6M-phosphate buffer (pH 6.0), and milliliter of a 5% (w/v) aqueous solution containing as a saccharide 50 mg, d.s.b., of α-maltosyl α,α-trehalose prepared by the method in Experiment 1-1, maltotetraose produced by Hayashibara Biochemical Laboratories, Inc., Okayama, Japan, or sucrose, were respectively placed in four 20-ml vials. These vials were sealed with butyl rubber bungs, placed in a thermostat controlled at 25° C., and irradiated with a 3,200 lux illumination using a fluorescent lamp. These vials were sampled in a time-dependent manner and the linoleic acid contained in each vials was quantified on GLC after methyl esterification: To each vial 20 ml of a mixture solution of chloroform and methanol (=2:1 by volume) was added to extract linoleic acid, and one milliliter of any of the extracts was placed in a 10-ml egg-plant type flask, concentrated in vacuo, and dried. To each of the resulting residues was added one milliliter solution of 30 mg/ml of 1-eicosanol in methanol as an internal standard substance, mixed to dissolve, dried again, admixed with one milliliter of a boron trifluoride methanol solution, sealed, and allowed to react for five minutes in a boiling water bath. After cooling, one milliliter of deionized water was added to the resulting each of the reaction mixtures to decompose the remaining boron trifluoride, admixed with one milliliter of n-hexane to extract methyl ester linoleate. Two micromilliliters of the n-hexane phase was sampled and subjected to GLC analysis. The decomposition percentage (%) of linoleic acid induced by light irradiation was calculated based on the contents of linoleic acid before and after the light irradiation by using the following equation. As a control, a system was provided and treated similarly as above except for adding no saccharide to the system.

Equation 1:

$$\text{Decomposition percentage (\%)} = \frac{A - B}{A} \times 100$$

Note: "A" means the content of linoleic acid before light irradiation. "B" means the content of linoleic acid after light irradiation.

In this analysis, the following apparatuses and conditions were used: "GC-14B", an apparatus for GLC commercialized by Shimadzu Corporation, Tokyo, Japan; "TC-FFAP", a capillary column for analysis, 0.53 mm in diameter, 30 m in length, and 1.0 μm thickness, commercialized by GL Sciences Inc., Tokyo, Japan; helium gas as a carrier gas at a flow rate of 10 ml/min; 230° C. as an injection temperature; as the conditions of column oven temperature after keeping at 120° C. for two minutes, it was heated up to 230° C. at a rate of 5° C./min; and a hydrogen flame ionization detector as a detector.

The results are tabulated in Table 9.

TABLE 9

| Saccharide | Decomposition percentage of linoleic acid (%) | | | |
| --- | --- | --- | --- | --- |
|  | 1 day | 4 days | 7 days | 14 days |
| None | 20.9 | 30.0 | 47.3 | 57.1 |
| α-Maltosyl α,α-trehalose | 6.1 | 20.6 | 30.5 | 40.6 |
| Maltotetraose | 17.8 | 29.8 | 46.8 | 56.9 |
| Sucrose | 15.4 | 32.1 | 50.2 | 57.5 |

As evident from the results in Table 9, it was revealed that, with respect to the influence of the decomposition of linoleic acid by light irradiation, the system coexisted with α-maltosyl α,α-trehalose was superior to the control system with no saccharide because it gave a lower decomposition level of linoleic acid than that of the control system and significantly inhibited the decomposition of linoleic acid. Maltotetraose and sucrose gave substantially no significant effect.

Experiment 7

Influence of the Coexisted Saccharides on the Decomposition of Linoleic Acid when Heated One hundred milligrams of linoleic acid, 0.5 g of a cellulose powder, 0.25 ml of 0.6M-phosphate buffer (pH 6.0), and one milliliter of a 0 to 10% (w/v) aqueous solution, containing as a saccharide 0, 12.5, 5, 25.0, 50.0 or 100.0 mg, d.s.b., of α-maltosyl α,α-trehalose prepared by the method in Experiment 1-1, maltotetraose produced by Hayashibara Biochemical Laboratories, Inc., Okayama, Japan, were respectively placed in four 20-ml vials. These vials were sealed with butyl rubber bungs, heated at 100° C. for one hour, and cooled to ambient temperature. Similarly as in Experiment 6, the linoleic acid in each vial was quantified on GLC before and after the heat treatment. In accordance with the method in Experiment 6, the decomposition percentage (%) of linoleic acid by heating was calculated based on the amounts of linoleic acid before and after the heat treatment.

The results are tabulated in Table 10.

TABLE 10

| Saccharide | Amount of saccharide added (mg) | Decomposition percentage of linoleic acid (%) |
| --- | --- | --- |
| α-Maltosyl α,α-trehalose | — | 58.6 |
|  | 12.5 | 46.4 |
|  | 25.0 | 35.2 |
|  | 50.0 | 28.1 |
|  | 100.0 | 10.5 |
| Maltotetraose | 12.5 | 57.5 |
|  | 25.0 | 57.2 |
|  | 50.0 | 56.0 |
|  | 100.0 | 58.4 |

As evident from the results in Table 10, it was revealed that, with respect to the influence of the decomposition of linoleic acid by heating, the system coexisted with α-maltosyl α,α-trehalose was superior to the control system with no saccharide because it gave a lower decomposition level of linoleic acid than that of the control system and significantly inhibited the decomposition of linoleic acid. It was also revealed that the inhibitory level positively increased as the increase of the amount of the α-maltosyl α,α-trehalose added; the decomposition level of linoleic acid was inhibited by less than ½ of that of the control when the saccharide was added in an amount of at least 50 mg. The system coexisted with maltotetraose showed substantially no such inhibitory effect.

Experiment 8

Influence of the Coexisted Saccharides on the Decomposition of Highly Unsaturated Fatty Acids when Heated Similarly as the method in Experiment 7, test samples were prepared and subjected to heat treatment, except for using a half milliliter of a methanol solution containing 100 mg of eicosapentaenoic acid or docosahexaenonic acid as a highly unsaturated fatty acid, and one milliliter of a 5% (w/v) aqueous solution, containing as a saccharide 50 mg, d.s.b., of α-maltosyl α,α-trehalose, prepared by the method in Experiment 1-1, or maltotetraose produced by Hayashibara Biochemical Laboratories, Inc., Okayama, Japan. In accordance with the method in Experiment 6, the highly unsaturated fatty acids before and after the heat treatment were quantified on GLC, and the decomposition percentage (%) of highly unsaturated fatty acids when heated was calculated based on the levels of highly unsaturated fatty acids before and after the heat treatment.

The results are tabulated in Table 11.

TABLE 11

| Saccharide | Decomposition percentage (%) of highly unsaturated fatty acids | |
|---|---|---|
| | Eicosapentaenoic acid | Docosahexaenoic acid |
| None | 26.3 | 25.8 |
| α-Maltosyl α,α-trehalose | 19.2 | 17.5 |
| Maltotetraose | 25.7 | 25.5 |

As evident from the results in Table 11, it was revealed that, with respect to the influence of the decomposition of highly unsaturated fatty acids by heating, the system coexisted with α-maltosyl α,α-trehalose was superior to the control system with no saccharide because it gave a lower decomposition level of highly unsaturated fatty acids than that of the control system and inhibited the decomposition of highly unsaturated fatty acids. While the system coexisted with maltotetraose showed no such inhibitory action.

Experiment 9

Influence of the Coexisted Saccharides on the Decomposition of Fatty Acids by Heating Similarly as the method in Experiment 6, test samples were prepared and subjected to heat treatment, except for using 100 mg of α-linolenic acid, linoleic acid, oleic acid or stearic acid as a fatty acid; and one milliliter of a 5% (w/v) of aqueous solution, containing as a saccharide 50 mg, d.s.b., of α-maltosyl α,α-trehalose, α-maltotriosyl α,α-trehalose, α-maltotetraosyl α,α-trehalose, or α-maltopentaosyl α,α-trehalose; or a material saccharide, used for preparing the above α-oligoglucosyl α,α-trehalose, such as maltotetraose, maltopentaose, maltohexaose, or maltoheptaose, which were all produced by Hayashibara Biochemical Laboratories, Inc., Okayama, Japan; or α,α-trehalose produced by Hayashibara Biochemical Laboratories, Inc., Okayama, Japan. In accordance with the method in Experiment 7, the fatty acids before and after the heat treatment were quantified on GLC. Then, in accordance with the method in Experiment 6, the decomposition percentage (%) of fatty acids when heated was calculated based on the levels of fatty acids before and after the heat treatment.

The results are tabulated in Table 12.

TABLE 12

| Saccharide | Decomposition percentage (%) of fatty acid | | | |
|---|---|---|---|---|
| | α-Linolenic acid | α-Linoleic acid | Oleic acid | Stearic acid |
| None | 47.9 | 58.6 | 29.9 | 11.2 |
| α-Maltosyl α,α-trehalose | 34.7 | 28.1 | 11.3 | 6.8 |
| α-Maltotriosyl α,α-trehalose | 35.2 | 29.5 | 10.8 | 7.5 |
| α-Maltotetraosyl α,α-trehalose | 36.8 | 31.2 | 12.5 | 7.1 |
| α-Maltopentaosyl α,α-trehalose | 36.5 | 31.5 | 13.7 | 7.8 |
| Maltotetraose | 46.5 | 56.0 | 29.8 | 11.3 |
| Maltopentaose | 47.8 | 59.3 | 30.1 | 11.1 |
| Maltohexaose | 48.3 | 58.1 | 29.5 | 11.5 |
| Maltoheptaose | 47.8 | 57.8 | 28.8 | 12.0 |
| α,α-Trehalose | 35.4 | 22.3 | 12.2 | 6.5 |

As evident from the results in Table 12, it was revealed that, with respect to the influence of the decomposition of fatty acids by heating, the system coexisted with an oligoglucosyl α,α-trehalose such as α-maltosyl α,α-trehalose, α-maltotriosyl α,α-trehalose, α-maltotetraosyl α,α-trehalose, or α-maltopentaosyl α,α-trehalose was superior to the control system with no saccharide because it gave a lower decomposition level of fatty acids than that of the control system and significantly inhibited the decomposition of fatty acids. These decomposition inhibitory actions by these α-oligoglucosyl α,α-trehaloses were revealed to have substantially the same level of inhibitory action as that of α,α-trehalose. While the system coexisted with maltotetraose, maltopentaose, maltohexaose, or maltoheptaose exhibited no such inhibitory action.

Experiment 10

Influence of the Coexisted Saccharides on the Rancidity of Products Containing Fatty Acids Using a mayonnaise as a product containing fatty acids, the influence of coexisted saccharides on the change of the quality of mayonnaise when stored under light irradiation conditions was examined as follows: Twenty parts by weight a commercialized mayonnaise were admixed with one part by weight of a saccharide to dissolve the saccharide in the mayonnaise. The saccharides used were α-maltosyl α,α-trehalose prepared by the method in Experiment 1-1, and maltotetraose produced by Hayashibara Biochemical Laboratories, Inc., Okayama, Japan. Twenty grams of each of the resulting mayonnaises were respectively placed in a transparent polyethylene bag, 120 mm×85 mm and 0.04 mm in thickness. NNN The bags were placed in a thermostat controlled at 25° C. and irradiated at an illuminance of 9,300 lux by using a fluorescent lamp. The specimens in the bags were sampled in a time-dependent manner and measured for the amount of volatile aldehydes, the peroxide value, and the carbonyl value as indicated below: The amount of volatile aldehydes was measured by placing three grams of a sample in a 20-ml vial, sealed with a butyl rubber bung, heated for five minutes in an aluminum block preheated at 80° C., followed by sampling two milliliters of HSG from the vial with a gas syringe and subjecting the sampled HSG to GLC analysis. In this analysis, the following apparatuses and conditions were used: "GC-14B", an apparatus for GLC commercialized by Shimadzu Corporation, Tokyo, Japan; "SPERUCO-WAX", a capillary column for analysis, 0.25 mm in diameter, 60 m in length, and 0.25 μm thickness, commercialized by Supelco Inc., USA; helium gas as a carrier gas at a flow rate of 1.0 ml/min; 250° C. as an injection temperature; as the conditions of column oven temperature after keeping at 80° C. for five minutes, it was heated up to 240° C. at a rate of 5° C./min; and a hydrogen flame ionization detector as a detector. The peroxide value and the carbonyl value of the samples were measured by treating the samples in accordance with the method disclosed in Method of Analysis in Health Science 1990, edited by Pharmaceutical Society of Japan, published by Kanehara & Co., Ltd., Tokyo, Japan, in 1990; and then subjecting the resulting samples to the method for peroxide value disclosed in chapter 2.4.12-71 and to the method for carbonyl value disclosed in chapter 2.4.22-73 in "Kijun-Yushi-Bunseki-Shiken-Ho" (Standard method for analysis of oils and fats). Similarly as above, a control system was prepared except for omitting the addition of saccharide and treated similarly as above. The data on the amount of volatile aldehydes, the peroxide value, and the carbonyl value are respectively tabulated in Tables 13, 14 and 15.

TABLE 13

| | | Amount of volatile aldehydes in HSG (μg/g sample) | | | | | | | | | |
|---|---|---|---|---|---|---|---|---|---|---|---|
| X | Y | Ethanal | Propanal | Butanal | Pentanal | Hexanal | Heptanal | Octanal | Nonanal | Decanal | Total |
| 3 | None | 0.0 | 89.6 | 0.0 | 0.0 | 1.9 | 0.0 | 3.0 | 6.1 | 2.1 | 102.7 |
|   | G2T* | 0.0 | 33.4 | 16.9 | 0.0 | 0.0 | 0.0 | 0.6 | 0.9 | 0.0 | 51.8 |
|   | G4** | 0.0 | 88.2 | 0.2 | 0.0 | 1.8 | 0.0 | 2.9 | 6.3 | 2.0 | 101.4 |
| 7 | None | 15.6 | 222.8 | 0.0 | 27.6 | 0.0 | 0.0 | 3.0 | 2.8 | 0.0 | 271.8 |
|   | G2T* | 0.0 | 39.8 | 16.3 | 6.4 | 0.0 | 0.0 | 0.6 | 1.2 | 0.0 | 64.3 |
|   | G4** | 15.8 | 241.5 | 0.8 | 28.2 | 0.0 | 0.0 | 3.0 | 2.9 | 0.0 | 292.2 |

*G2T; α-Maltosyl α,α-trehalose
**G4; Maltotetraose
X: Storage period (day)
Y: Saccharide

TABLE 14

| | Peroxide value (meq/kg oils and fats) | | |
|---|---|---|---|
| Saccharide | Initiation day of storing | Three days after storing | Seven days after storing |
| None | 0.0 | 34.0 | 156.8 |
| α-Maltotetraosyl α,α-trehalose | 0.1 | 24.5 | 98.1 |
| Maltotetraose | 0.1 | 34.2 | 169.1 |

TABLE 15

| | Carbonyl value* | | |
|---|---|---|---|
| Saccharide | Initiation day of storing | Three days after storing | Seven days after storing |
| None | 2.0 | 7.5 | 42.3 |
| α-Maltotetraosyl α,α-trehalose | 2.3 | 7.3 | 28.5 |
| Maltotetraose | 2.2 | 9.4 | 43.9 |

Note:
The symbol "*" means an absorbance at 440 nm per one gram of a sample.

As evident from the results in Tables 13, 14 and 15, the systems coexisted with α-maltosyl α,α-trehalose gave lower levels of volatile aldehyde amount, peroxide value, and carbonyl value than those of the system with no saccharide. Thus the degree of rancidity of mayonnaise was inhibited by the coexistence of α-maltosyl α,α-trehalose. These results indicate that the coexistence of α-maltosyl α,α-trehalose well inhibits the rancidity of fatty acid-containing products such as mayonnaise when the products are stored under light irradiation conditions.

Experiment 11

Influence of the Coexistence of Saccharides on the Rancidity of Products Containing Fatty Acids The influence of the coexistence of saccharides on the rancidity of products containing fatty acids was examined by storing a fried carrot, which contained α-maltosyl α,α-trehalose or maltotetraose, as a fatty acid-containing product, at 40° C. for 14 days: A carrot was pealed and cut by a slicer into pieces about 5 mm in thickness, followed by branching the pieces for three minutes in a hot water (95° C.) containing 18% of α-maltosyl α,α-trehalose or maltotetraose. Another carrot was branched similarly as above in the absence of saccharide for use as a control. These specimens were in a usual manner fried in an edible oil under a reduced pressure to obtain a fried carrot containing α-maltosyl α,α-trehalose or maltotetraose, and as a control another one with no saccharide. Five grams aliquots of the fried carrot thus obtained were placed in a 20-ml vial, sealed with a butyl rubber bung, and stored in a thermostat controlled at 40° C. for 14 days under light-shielded conditions. The amount of volatile aldehydes was measured on the initiation day of the storing test and 14 days after the initiation of the test after treating the fried carrots similarly as in Experiment 11. The results are in tabulated in Table 16.

TABLE 16

Amount of volatile aldehydes in HSG (μg/g sample)

| X | Y | Ethanal | Propanal | Butanal | Pentanal | Hexanal | Heptanal | Octanal | Nonanal | Total |
|---|---|---------|----------|---------|----------|---------|----------|---------|---------|-------|
| 0 | None | 0.00 | 0.31 | 0.08 | 0.20 | 0.09 | 0.00 | 0.00 | 0.00 | 0.71 |
|   | G2T* | 0.02 | 0.00 | 0.04 | 0.00 | 0.00 | 0.00 | 0.00 | 0.00 | 0.06 |
|   | G4** | 0.00 | 0.00 | 1.28 | 1.08 | 0.04 | 0.03 | 0.03 | 0.00 | 2.46 |
| 14 | None | 5.01 | 0.00 | 24.32 | 0.00 | 0.00 | 0.31 | 0.00 | 0.00 | 29.64 |
|   | G2T* | 0.00 | 0.02 | 8.52 | 0.00 | 0.00 | 0.00 | 0.00 | 0.00 | 8.54 |
|   | G4** | 2.32 | 2.11 | 11.35 | 0.00 | 0.00 | 0.10 | 0.00 | 0.05 | 15.93 |

*G2T; α-Maltosyl α,α-trehalose
**G4; Maltotetraose
X: Storage period (day)
Y: Saccharide As evident from the results in Table 16, it was revealed that the formation level of volatile aldehydes from fried carrots was modified by the coexistence of saccharides and their kinds during frying and storing after such frying. It was also revealed that the system coexisted with α-maltosyl α,α-trehalose less formed volatile aldehydes and more effectively inhibited the formation of volatile aldehydes than those coexisted with no saccharide or with maltotetraose.

Experiment 12

Influence of the Coexistence of Saccharides on the Rancidity of Fatty Acid-Containing Products To examine the influence of the coexistence of saccharides on the rancidity of fatty acid-containing products, doughnuts as fatty acid-containing products, which contained α-maltosyl α,α-trehalose and/or sucrose, were stored at 30° C. for 7 or 14 days. A doughnut dough, containing α-maltosyl α,α-trehalose and/or sucrose, was prepared based on the composition in Table 17 and fried in a usual manner to obtain doughnuts. They were sprayed with one gram of a 50% aqueous solution of sucrose or α-maltosyl α,α-trehalose per doughnut, about six grams each, just after processing, and four pieces of each type of doughnut were placed in an aluminum laminated bag, 17×10 cm, followed by injecting air into the bag to give an air volume of about 200 ml, sealing the bag, and storing the doughnuts at 30° C. for 7 or 14 days under light-shielded conditions.

TABLE 17

|  |  | Test group No. | | | |
|---|---|---|---|---|---|
|  |  | 1 (Control) | 2 | 3 | 4 |
| Composition | Wheat flour | 300 | 300 | 300 | 300 |
|  | White soft sugar | 90 | 40 | 40 | 90 |
|  | α-Maltosyl α,α-trehalose | 0 | 54 | 54 | 0 |
|  | Egg | 100 | 100 | 100 | 100 |
|  | Butter | 30 | 30 | 30 | 30 |
|  | Baking powder | 10 | 10 | 10 | 10 |
|  | Water | 60 | 56 | 56 | 60 |
| Sprayed aqueous saccharide solution |  | Sucrose | Sucrose | α-Maltosyl α,α-trehalose | α-Maltosyl α,α-trehalose |

Note:
In the table, each numeral means a part by weight of a dough for doughnut.
α-Maltosyl α,α-trehalose had a moisture content of about 7.2%.

The amount of volatile aldehydes was measured by placing bags in an electric oven preheated at 80° C. on the initiation day of the storing test, and 7 and 14 days after the initiation of the test, keeping the bags in the oven at 80° C. for five minutes, sampling two milliliters of HSG from each bag, and subjecting to GLC analysis similarly as in Experiment 11. The results are tabulated in Table 18.

TABLE 18

| Storage period (day) | Test No. | Amount of volatile aldehydes in HSG (μg/g sample) | | | | | | | | | |
|---|---|---|---|---|---|---|---|---|---|---|---|
|  |  | Ethanal | Propanal | Butanal | Pentanal | Hexanal | Heptanal | Octanal | Nonanal | Decanal | Total |
| 0 | No. 1 | 2.17 | 0.00 | 0.11 | 2.72 | 0.00 | 0.00 | 0.00 | 0.10 | 0.00 | 5.10 |
|  | No. 2 | 1.52 | 0.00 | 0.05 | 1.03 | 0.00 | 0.00 | 0.05 | 0.00 | 0.00 | 2.65 |
|  | No. 3 | 0.58 | 0.00 | 0.00 | 0.62 | 0.00 | 0.00 | 0.05 | 0.05 | 0.00 | 1.30 |
|  | No. 4 | 1.33 | 0.00 | 0.10 | 0.82 | 0.00 | 0.00 | 0.10 | 0.05 | 0.00 | 2.40 |

TABLE 18-continued

| Storage period (day) | Test No. | Amount of volatile aldehydes in HSG (μg/g sample) | | | | | | | | | |
|---|---|---|---|---|---|---|---|---|---|---|---|
| | | Ethanal | Propanal | Butanal | Pentanal | Hexanal | Heptanal | Octanal | Nonanal | Decanal | Total |
| 7 | No. 1 | 0.00 | 4.84 | 4.52 | 2.03 | 0.47 | 0.00 | 0.05 | 0.31 | 0.00 | 12.22 |
| | No. 2 | 1.01 | 0.50 | 2.19 | 1.54 | 2.23 | 0.05 | 0.05 | 0.00 | 0.05 | 7.62 |
| | No. 3 | 0.58 | 0.32 | 1.05 | 1.73 | 1.57 | 0.18 | 0.05 | 0.00 | 0.05 | 5.53 |
| | No. 4 | 0.00 | 1.25 | 2.84 | 1.87 | 0.53 | 0.00 | 0.05 | 0.10 | 0.00 | 6.64 |
| 14 | No. 1 | 0.00 | 4.35 | 9.94 | 5.91 | 0.75 | 0.00 | 0.41 | 0.00 | 0.00 | 21.36 |
| | No. 2 | 1.13 | 0.52 | 2.87 | 2.35 | 2.58 | 0.12 | 0.20 | 0.05 | 0.15 | 9.97 |
| | No. 3 | 0.33 | 0.23 | 1.34 | 2.03 | 1.87 | 0.11 | 0.05 | 0.00 | 0.15 | 6.11 |
| | No. 4 | 0.00 | 1.38 | 3.21 | 1.96 | 0.73 | 0.00 | 0.05 | 0.10 | 0.00 | 7.43 |

As evident from the results in Table 18, it was revealed that the formation level of volatile aldehydes from doughnuts was differently modified depending on the kind of coexisted saccharides. It was also revealed that the system coexisted with α-maltosyl α,α-trehalose less formed volatile aldehydes and more effectively inhibited the formation of volatile aldehydes than that coexisted with sucrose or a white soft sugar.

Particularly, it was revealed that the formation inhibitory effect on volatile aldehydes by α-maltosyl α,α-trehalose will be exerted whenever the saccharide is incorporated into a dough for doughnut or an aqueous α-maltosyl α,α-trehalose solution is sprayed over the surface of doughnuts just after processing without incorporating into such dough. While, the doughnut, which had been prepared by incorporating α-maltosyl α,α-trehalose into a dough and then spraying the above aqueous solution over the doughnut just after processing, had the lowest formation level of volatile aldehydes and a satisfactory shelf-life.

Experiment 13

Influence of Saccharides Containing α-maltosyl α,α-trehalose on the Formation of Fish Smell It is said that one of the causatives of fish smell is volatile aldehydes occurred as a result of deterioration/rancidity of fish meat. Accordingly, the following experiment was conducted to examine the influence of α-maltosyl α,α-trehalose on the formation of volatile aldehydes.

Experiment 13-1

Preparation of Test Samples

Commercially available mackerels were removed their head, intestine, and bone parts and subjected to a mincer to obtain a minced mackerel. The mince thus obtained was further kneaded to homogeneity, and five grams of which were placed in a 20-ml vial and admixed with five milliliters of a syrup containing α-oligoglucosyl α,α-trehaloses, prepared by the method in the later described Example A-1, or of an aqueous solution containing 5%, d.s.b., of sucrose, a commercially available granulated sugar. The resulting vials were sealed with butyl rubber bungs for use as test samples. As control samples, similarly as above, five grams of the above minced mackerel were placed in a vial and admixed with five milliliters of deionized water, followed by sealing the vial with a butyl rubber bung. These test control samples were heated in a boiling water for 15 min and then cooled in a flowing water. Thereafter, these samples were reheated at 80° C. for 5 min, and the amount of volatile aldehydes in HSG in each vial was measured.

Experiment 13-2

Measurement for the Amount of Volatile Aldehydes

The amount of volatile aldehydes was measured by using the following sample, apparatuses, and conditions: As a sample, two milliliters of HSG was used; "TC-FFAP", a capillary column for analysis, 0.52 mm in diameter, 30 m in length, and 1 μm (=df), split ratio of 1/30, commercialized by GL Sciences Inc., Tokyo, Japan; "GC-14B", a hydrogen flame ionization detector for GLC commercialized by Shimadzu Corporation, Tokyo, Japan; helium gas as a carrier gas at a flow rate of 1 ml/min; and an increasing temperature rate of 5° C./min from 40 to 250° C. The measured volatile aldehydes were nine aldehydes as listed in Table 19, and the amounts measured were summed to give a total aldehyde amount.

The amount of generated volatile aldehydes for each control sample was regarded as 100, and based on this the amount of the formed aldehydes for each test sample was expressed with a relative value. The results are in Table 19.

TABLE 19

| | Saccharide | | |
|---|---|---|---|
| Volatile aldehydes | With no saccharide (Control) | Sucrose | α-Oligoglucosyl α,α-trehalose syrup |
| Acetaldehyde | 100 | 87 | 46 |
| Propanal | 100 | 68 | 4 |
| Butanal | 100 | 113 | 0 |
| Pentanal | 100 | 115 | 0 |
| Hexanal | 100 | 67 | 0 |
| Heptanal | 100 | 46 | 5 |
| Octanal | 100 | 57 | 32 |
| Nonanal | 100 | 154 | 0 |
| Decanal | 100 | 43 | 31 |
| Total aldehydes | 100 | 80 | 32 |

As evident from the results in Table 19, the test samples with the syrup of α-oligoglucosyl α,α-trehaloses more effectively inhibited the formation of volatile aldehydes from minced mackerel by heating when compared with the control samples. While the test samples with sucrose gave a somewhat lower level of total volatile aldehydes as compared with the control samples, however, some of the test samples showed an adverse increase with respect to some types of volatile aldehydes. Based on these, it was revealed that α-oligoglucosyl α,α-trehaloses even in the form of a saccharide mixture containing such saccharides and others effectively inhibit the formation of volatile aldehydes from compositions such as fish meat, and that they can be used to reduce the level of unfavorable or undesirable smell such as fish smell induced by volatile aldehydes generated from compositions such as fish meat.

The following Examples A and B explain the present invention in more detail with reference to the preferred embodiments of the agents for inhibiting the formation of volatile aldehydes and/or the decomposition of fatty acids, and the compositions containing fatty acids, respectively.

Example A-1

To a 20% corn starch suspension was mixed with calcium carbonate to give the final concentration of 0.1%, and the resultant mixture was adjusted to pH 6.5, admixed with 0.2% per g starch of "TERMAMYL 60L", an α-amylase specimen commercialized by Novo Industri A/S Copenhagen Denmark, and subjected to an enzymatic reaction at 95° C. for 15 min. The reaction mixture was autoclaved at 120° C. for 10 min, cooled to 50° C., adjusted to pH 5.8, admixed with five units per g starch of a maltotetraose-forming amylase, disclosed in Japanese Patent Kokai No. 240,784/88, commercialized by Hayashibara Biochemical Laboratories, Inc., Okayama, Japan, and 500 units per g of an isoamylase specimen commercialized by Hayashibara Biochemical Laboratories, Inc., Okayama, Japan, and subjected to an enzymatic reaction for 48 hours. The resultant mixture was admixed with 30 units/g starch of "α-AMYLASE 2A", an α-amylase specimen commercialized by Ueda Chemical Co., Ltd., Osaka, Japan, and subjected to an enzymatic reaction at 65° C. for four hours. The reaction mixture was autoclaved at 120° C. for 10 min, cooled to 45° C., admixed with two units/g starch of a non-reducing saccharide-forming enzyme from *Arthrobacter* sp. Q36 (FERM BP-4316) disclosed in Japanese Patent Kokai No. 143,876/95, and subjected to an enzymatic reaction for 48 hours. The resultant mixture was kept at 95° C. for 10 min, cooled, and filtered to obtain a filtrate which was then in a usual manner decolored with an activated charcoal, desalted with ion-exchange resins in H- and OH-forms, and purified, followed by concentrating the resultant solution to obtain a 70% syrup in a yield of about 90%, d.s.b. The product exhibited a DE of 13.7 and contained 52.5%, d.s.b., of α-maltosyl α,α-trehalose, 1.1%, d.s.b., of α-maltotriosyl α,α-trehalose, and 0.4%, d.s.b., of α-maltotetraosyl α,α-trehalose. The product can be advantageously used as an agent for inhibiting the formation of volatile aldehydes and/or the decomposition of fatty acids. Also, the product can be arbitrarily used as a substrate for pulverization, additive for preparations, adhesiveness-preventing agent for starch-containing foods, gloss-imparting agent, luster-imparting agent, shape-retaining agent, moisture-variation inhibitory agent, denaturation-preventing agent, color-change inhibitory agent for pigments, freshness-retaining agent, flavor/taste-retaining agent, and growth-promoting agent for plants.

Example A-2

A syrup prepared by the method in Example A-1 was in a usual manner spray-dried to obtain an amorphous powder. The product can be advantageously used as an agent for inhibiting the formation of volatile aldehydes and/or the decomposition of fatty acids. Also, since the product has a lower moisture absorbency and a satisfactory water solubility, it can be advantageously used as a substrate to pulverize juice, as well as oils and fats. The product can be arbitrarily used as an additive for preparations, adhesiveness-preventing agent for starch-containing foods, gloss-imparting agent, luster-imparting agent, shape-retaining agent, moisture-variation inhibitory agent, denaturation-preventing agent, color-change inhibitory agent for pigments, freshness-retaining agent, flavor/taste-retaining agent, and growth-promoting agent for plants.

Example A-3

A syrup prepared by the method in Example A-1 was fractionated using a column packed with "DOWEX 50W-X4", a strongly-acidic cation exchange resin commercialized by Dow Chemical Co., Midland, Mich., USA. The resin was packed in four jacketed-stainless steel columns having an inner diameter of 5.4 cm, and the columns were cascaded in series to give a total gel-bed depth of 20 m. The columns were heated to give the inner column temperature of 55° C., and fed with 5% (v/v) of the saccharide solution while keeping at the temperature, and the saccharide solution was fractionated by feeding to the columns with 55° C. hot water at an SV (space velocity) of 0.13 to separate fractions rich in glucose and maltose, followed by collecting fractions rich in α-oligoglucosyl α,α-trehaloses. The collected fractions were pooled, purified, concentrated, and spray-dried to obtain a powder rich in α-oligoglucosyl α,α-trehaloses in an amorphous form. The product contained 70.2%, d.s.b., of α-maltosyl α,α-trehalose, 2.1%, d.s.b., of α-maltotriosyl α,α-trehalose, and 1.1%, d.s.b., of α-maltotetraosyl α,α-trehalose. The product can be advantageously used as an agent for inhibiting the formation of volatile aldehydes and/or the decomposition of fatty acids.

Example A-4

One part by weight of potato starch was admixed with six parts by weight of water and "NEO-SPITASE™", an α-amylase specimen commercialized by Nagase Biochemicals, Ltd., Kyoto, Japan, in an amount of 0.01% per g starch, and the resultant suspension was adjusted to pH 6.0, heated to 85° C. to 90° C., and simultaneously gelatinized and liquefied at the temperature. Thereafter, the resultant was immediately heated to 120° C. for 5 min to keep the DE (dextrose equivalent) below 1.0, rapidly cooled to 55° C., adjusted to pH 7.0, admixed with 150 units/g starch of "PULLULANASE (EC 3.2.1.41)", an enzyme specimen commercialized by Hayashibara Biochemical Laboratories, Inc., Okayama, Japan, and eight units/g starch of a maltotetraose-forming enzyme disclosed in Japanese Patent Kokai No. 240,784/88, and subjected to an enzymatic reaction at pH 7.0 and 50° C. for 36 hours. The reaction mixture was autoclaved at 120° C. for 10 min, cooled to 53° C., admixed with two units/g starch of a non-reducing saccharide-forming enzyme derived from *Arthrobacter* sp. S34 (FERM BP-6450) disclosed in Japanese Patent Kokai No. 2000-228,980, and subjected to an enzymatic reaction for 64 hours. The reaction mixture was heated at 95° C. for 10 min, cooled, and filtered. The resultant filtrate was in a usual manner decolored with an activated charcoal, desalted with ion-exchange resins in H- and OH-forms, and purified. The resultant solution was concentrated and spray-dried to obtain a powder rich in α-oligoglucosyl α,α-trehaloses in an amorphous form in a yield of about 90%, d.s.b. The product had a DE of 11.4 and contained 62.5%, d.s.b., of α-maltosyl α,α-trehalose, 0.8%, d.s.b., of α-maltotriosyl α,α-trehalose, and 0.5%, d.s.b., of α-maltotetraosyl α,α-trehalose. The product can be advantageously used as an agent for inhibiting the formation of volatile aldehydes and/or the decomposition of fatty acids.

Example A-5

A 20% solution of a reagent grade maltotetraose, with a purity of at least 97.0%, commercialized by Hayashibara Biochemical Laboratories, Inc., Okayama, Japan, was adjusted to pH 7.0, admixed with two units/g saccharide, d.s.b., of a non-reducing saccharide-forming enzyme disclosed in Japanese Patent Kokai No. 143,876/95, and subjected to saccharifying reaction at 46° C. for 48 hours to obtain a solution containing 79.8%, d.s.b, of α-maltosyl α,α-trehalose. The reaction mixture was adjusted to pH 6.0, admixed with 10 units/g saccharide, d.s.b., of a β-amylase specimen produced by Nagase Biochemicals, Ltd., Kyoto, Japan, and subjected to enzymatic reaction at 50° C. for 48 hours to hydrolyze maltotetraose. The resulting reaction mixture was autoclaved at 120° C. for 10 min, cooled, and filtered. The filtrate was fractionated using "XT-1016 ($Na^+$-form, polymerization degree of 4%)", an alkaline-metal strongly-acidic action exchange resin commercialized by Tokyo Organic Chemical Industries, Ltd., Tokyo, Japan, followed by collecting fractions rich in α-maltosyl α,α-trehalose, pooled, purified, concentrated, and sprayed-dried to obtain a powder rich in α-maltosyl α,α-trehalose in an amorphous form. The product contained 98.1%, d.s.b., of α-maltosyl α,α-trehalose and had a reducing power lower than the detectable level when determined on the Somogyi-Nelson's method. The product can be advantageously used as an agent for inhibiting the formation of volatile aldehydes and/or the decomposition of fatty acids. Also, since the product does not substantially have reducibility, it can be suitably used as an agent for inhibiting the formation of volatile aldehydes and/or the decomposition of fatty acids in health foods, cosmetics, quasi-drugs, pharmaceuticals, feeds, baits, and chemical/industrial products, which all contain ingredients, for example, compounds with amino acids or amino groups, that are problematically inactivated by the Maillard reaction.

The above product was dissolved in water again, treated with an activated charcoal, treated to remove pyrogen, and spray-dried to obtain a powder rich in α-maltosyl α,α-trehalose in an amorphous form. The product thus obtained can be advantageously used as an agent for inhibiting the formation of volatile aldehydes and/or the decomposition of fatty acids. Since the product has no pyrogen, it can be suitably used, particularly, as an agent for pharmaceuticals.

Example A-6

To a syrup containing α-oligoglucosyl α,α-trehaloses obtained by the method in Example A-1 was added water to obtain an about 60% aqueous solution, followed by placing the solution in an autoclave, adding thereto the Raney nickel as a catalysis in an amount of about 8.5%, and hydrogenating the reducing saccharides such as glucose and maltose coexisted with α-oligoglucosyl α,α-trehaloses to convert the reducing saccharides into sugar alcohols while stirring, increasing the inner temperature to 128° C., and increasing the inner hydrogen pressure to 80 kg/$cm^2$. After the conversion reaction, the remaining Raney nickel was removed from the reaction mixture, and the resulting mixture was decolored, desalted, purified, and concentrated into a syrup. The product can be advantageously used as an agent for inhibiting the formation of volatile aldehydes and/or the decomposition of fatty acids. Also, the product does not substantially have reducibility and it can be suitably used as an agent for inhibiting the formation of volatile aldehydes and/or the decomposition of fatty acids in cosmetics, quasi-drugs, pharmaceuticals, and health foods, which all contain ingredients that are problematically inactivated by the Maillard reaction. The product can be arbitrarily used as a substrate for pulverization, additive for preparations, adhesiveness-preventing agent for starch-containing foods, gloss-imparting agent, luster-imparting agent, shape-retaining agent, moisture-variation inhibitory agent, denaturation-preventing agent, color-change, inhibitory agent for pigments, freshness-retaining agent, flavor/taste-retaining agent, and growth-promoting agent for plants.

Example A-7

A powder containing α-oligoglucosyl α,α-trehaloses in an amorphous form, obtained by the method in Example A-3, was dissolved in water to obtain an about 60% solution, followed by placing the solution in an autoclave, admixing the Raney nickel as a catalysis in an amount of about 9%, hydrogenating the reducing saccharides such as glucose and maltose coexisted with α-oligoglucosyl α,α-trehaloses to convert into sugar alcohols while stirring, increasing the inner temperature to 130° C., and increasing the inner hydrogen pressure to 75 kg/$cm^2$. After the conversion reaction, the remaining Raney nickel was removed from the reaction mixture, and the resulting mixture was decolored, desalted, purified, and concentrated into a syrup. The syrup was spray-dried in a usual manner to obtain a powder in an amorphous form. The product can be advantageously used as an agent for inhibiting the formation of volatile aldehydes and/or the decomposition of fatty acids. Also, the product substantially does not substantially have reducibility and it can be suitably used as an agent for inhibiting the formation of volatile aldehydes and/or the decomposition of fatty acids in cosmetics, quasi-drugs, pharmaceuticals, and health foods, which all contain ingredients that are problematically inactivated by the Maillard reaction. The product can be arbitrarily used as a substrate for pulverization, additive for preparations, adhesiveness-preventing agent for starch-containing foods, gloss-imparting agent, luster-imparting agent, shape-retaining agent, moisture-variation inhibitory agent, denaturation-preventing agent, color-change inhibitory agent for pigments, freshness-retaining agent, flavor/taste-retaining agent, and growth-promoting agent for plants.

Example A-8

A 6% potato starch suspension was gelatinized by heating, adjusted to pH 4.5, heated to 50° C., admixed with 2,500 units/g starch of an isoamylase specimen produced by Hayashibara Biochemical Laboratories, Inc., Okayama, Japan, and enzymatically reacted for 20 hours. The reaction mixture was autoclaved at 120° C. for 10 min, cooled to 45° C., admixed with 150 units/g starch of "TERMAMYL 60L", an α-amylase specimen commercialized by Novo Industri A/S Copenhagen Denmark, and subjected to an enzymatic reaction for 24 hour. The reaction mixture was autoclaved at 120° C. for 20 min, cooled to 45° C., admixed with two units/g starch of a non-reducing saccharide-forming enzyme from *Arthrobacter* sp. Q36 (FERM BP-4316) disclosed in Japanese Patent Kokai No. 143,876/95, and subjected to an enzymatic reaction for 64 hours. The resultant mixture was kept at 95° C. for 10 min, cooled, and filtered to obtain a filtrate which was then in a usual manner decolored with an activated charcoal, desalted with ion-exchange resins in H- and OH-forms, purified, and concentrated to obtain a 65% α-oligoglucosyl α,α-trehalose syrup in a yield of about 89%, d.s.b. The product exhibited contained 6.5%, d.s.b., of α-maltosyl α,α-trehalose, 28.5%, d.s.b., of α-maltotriosyl α,α- trehalose, 4.1%, d.s.b., of α-maltotetraosyl α,α-trehalose, and 1.5%, d.s.b., of α-maltopentaosyl α,α-trehalose. The product can be advantageously used as an agent for inhibiting the formation of volatile aldehydes and/or the decomposition of fatty acids. Also, the product can be arbitrarily used as a substrate for pulverization, additive for preparations, adhesiveness-preventing agent for starch-containing foods, gloss-imparting agent, luster-imparting agent, shape-retaining agent, moisture-variation inhibitory agent, denaturation-preventing agent, color-change inhibitory agent for pigments, freshness-retaining agent, flavor/taste-retaining agent, and growth-promoting agent for plants.

In accordance with the method in Example A-7, the product thus obtained was hydrogenated to convert the reducing saccharides such as glucose and maltose, coexisted with α-oligoglucosyl α,α-trehaloses, into sugar alcohols, and purified in a usual manner to obtain a syrup. The product can be advantageously used as an agent for inhibiting the formation of volatile aldehydes and/or the decomposition of fatty acids. Also, the product substantially does not substantially have reducibility and it can be arbitrarily used as an agent for inhibiting the formation of volatile aldehydes and/or the decomposition of fatty acids in cosmetics, quasi-drugs, pharmaceuticals, and health foods, which all contain ingredients that are problematically inactivated by the Maillard reaction. Also the product can be arbitrarily used as a substrate for pulverization, additive for preparations, adhesiveness-preventing agent for starch-containing foods, gloss-imparting agent, luster-imparting agent, shape-retaining agent, moisture-variation inhibitory agent, denaturation-preventing agent, color-change inhibitory agent for pigments, freshness-retaining agent, flavor/taste-retaining agent, and growth-promoting agent for plants.

Example A-9

To a 33% corn starch suspension was added calcium carbonate to give a final concentration of 0.1%, and the resultant mixture was adjusted to pH 6.0, admixed with 0.2% per g starch of "TERMAMYL 60L", an α-amylase specimen commercialized by Novo Industri A/S Copenhagen Denmark, and subjected to an enzymatic reaction at 95° C. for 15 min. The reaction mixture was autoclaved at 120° C. for 30 min, cooled to 50° C., admixed with 500 units/g starch of an isoamylase specimen produced by Hayashibara Biochemical Laboratories, Inc., Okayama, Japan, and 1.8 units/g starch of a maltohexaose/maltoheptaose-forming amylase disclosed in Japanese Patent Kokai No. 236,478/95, and subjected to an enzymatic reaction for 40 hours. The resultant mixture was autoclaved at 120° C. for 10 min, cooled to 53° C., adjusted to pH 5.7, admixed with two units per g starch of a non-reducing saccharide-forming enzyme from *Arthrobacter* sp. S34 (FERM BP-6450) disclosed in Japanese Patent Kokai No. 2000-228,980, and subjected to an enzymatic reaction for 64 hours. The resultant mixture was kept at 95° C. for 10 min, cooled, and filtered to obtain a filtrate which was then in a usual manner decolored with an activated charcoal, desalted with ion-exchange resins in H- and OH-forms, and purified, followed by concentrating the resultant solution to obtain a powder containing α-oligoglucosyl α,α-trehaloses in an amorphous form, in a yield of 87%, d.s.b. The product contained 6.5%, d.s.b., of α-maltosyl α,α-trehalose, 5.6%, d.s.b., of α-maltotriosyl α,α-trehalose, 21.9%, d.s.b., of α-maltotetraosyl α,α-trehalose, and 9.3% of α-maltopentaosyl α,α-trehalose. The product can be arbitrarily used intact or after conventional purification for increasing the content of α-oligoglucosyl α,α-trehaloses, and in any case, it can be advantageously used as an agent for inhibiting the formation of volatile aldehydes and/or the decomposition of fatty acids. Also, the product can be arbitrarily used as a substrate for pulverization, additive for preparations, adhesiveness-preventing agent for starch-containing foods, gloss-imparting agent, luster-imparting agent, shape-retaining agent, moisture-variation inhibitory agent, denaturation-preventing agent, color-change inhibitory agent for pigments, freshness-retaining agent, flavor/taste-retaining agent, and growth-promoting agent for plants.

In accordance with the method in Example A-7, the product thus obtained was hydrogenated to convert the reducing saccharides such as glucose and maltose, coexisted with α-oligoglucosyl α,α-trehaloses, into sugar alcohols, and then purified in a usual manner and spray-dried to obtain a powder in an amorphous form. The product can be advantageously used intact or after conventional purification for increasing the content of α-oligoglucosyl α,α-trehaloses, and in any case, it can be advantageously used as an agent for inhibiting the formation of volatile aldehydes and/or the decomposition of fatty acids. Also, the product does not substantially have reducibility and it can be arbitrarily used as an agent for inhibiting the formation of volatile aldehydes and/or the decomposition of fatty acids in cosmetics, quasi-drugs, pharmaceuticals, and health foods, which all contain ingredients that are problematically inactivated by the Maillard reaction. In addition, the product can be arbitrarily used as a substrate for pulverization, additive for preparations, adhesiveness-preventing agent for starch-containing foods, gloss-imparting agent, luster-imparting agent, shape-retaining agent, moisture-variation inhibitory agent, denaturation-preventing agent, color-change inhibitory agent for pigments, freshness-retaining agent, flavor/taste-retaining agent, and growth-promoting agent for plants.

Example A-10

To 90 parts by weight of water were added 40 parts by weight of a syrup containing α-oligoglucosyl α,α-trehaloses obtained by the method in Example A-6, 0.1 part by weight of calcium chloride, and 0.2 part by weight of citric acid. The mixture was injected into a container, sterilized by heating, and cooled to obtain a syrupy product. The product can be advantageously used as an agent in the form of a syrup for inhibiting the formation of volatile aldehydes and/or the decomposition of fatty acids in preserving fatty acid-containing products and/or in processing materials for such products, particularly, in preserving edible parts of fishery/livestock products and/or in processing materials for such edible parts.

Example A-11

Twenty-five parts by weight of α-oligoglucosyl α,α-trehaloses obtained by the method in Example A-2, 25 parts by weight of anhydrous crystalline α,α-trehalose commercialized by Hayashibara Shoji, Inc., Okayama, Japan, and 50 parts by weight of salt were mixed to homogeneity into a powdery product. The product can be advantageously used as an agent in the form of a powder for inhibiting the formation of volatile aldehydes and/or the decomposition of fatty acids in preserving fatty acid-containing products and/or in processing materials for such products, particularly, in oily seasonings such as mayonnaises and dressings, and materials of seasonings such as roasted seeds, as well as materials for pickles with reduced salt for edible parts of fishery/livestock products.

Example A-12

Twenty parts by weight of α-oligoglucosyl α,α-trehaloses obtained by the method in Example A-3, two parts by weight of "DEXYPEARL®", a powder containing β-cyclodextrin commercialized by Hayashibara Shoji, Inc., Okayama, Japan, and one part by weight of pullulan were mixed to homogeneity. The resulting mixture was in a usual manner granulated with a granulator to obtain a product in the form of a granule. The product can be advantageously used as an agent in the form of a granule for inhibiting the formation of volatile aldehydes and/or the decomposition of fatty acids in preserving fatty acid-containing products and/or in processing materials for such products.

Example A-13

Twenty-five parts by weight of α-oligoglucosyl α,α-trehaloses obtained by the method in Example A-7, 25 parts by weight of "MABIT®", an anhydrous crystalline maltitol commercialized by Hayashibara Shoji, Inc., Okayama, Japan, one part by weight of pullulan, 0.1 part by weight of tartaric acid, and 0.1 part by weight malic acid were mixed to homogeneity. The resulting mixture was in a usual manner tabletted with a tabletting machine to obtain tablets, each having 8 mm in diameter and 4.5 mm in thickness. The product can be advantageously used as an agent in the form of a tablet for inhibiting the formation of volatile aldehydes and/or the decomposition of fatty acids in preserving fatty acid-containing products and/or in processing materials for such products, particularly, in cooking edible parts of fishery/livestock products to prepare daily dishes, cooked dishes in pots, etc.

Example B-1

Processed Product of Fish Eggs

An inhibitory agent, obtained by the method in Example A-10, was placed in a container and diluted with water by 5-times. Fresh herring roes were placed in a sieve basket which was then soaked in the above dilute. After one-hour standing, the herring roes were drained off by putting the sieve basket out of the dilute to obtain the captioned product. The product well inhibited the formation of volatile aldehydes and/or the decomposition of fatty acids, less changed in quality under cold storage, and less formed drip when thawed after cold storage. In both conditions, the product well kept its desired freshness. When cooked in a usual manner, the product less induced smell of volatile aldehydes and trimethylamine, and had a satisfactory flavor, taste, and mouth feel.

Example B-2

Dried Product

One hundred parts by weight of a raw puffer fillet were coated with three parts by weight of an inhibitory agent with salt obtained by the method in Example A-11, rolled to form a sheet, about eight millimeters in thickness. The sheet was soaked for 30 min in 200 parts by weight of an inhibitory agent obtained by the method in Example A-10, drained, and dried overnight to obtain the captioned product. The product was a dried product, which the formation of volatile aldehydes and/or the decomposition of fatty acids were well inhibited and the freshness was well retained. When grilled in a usual manner, the product less induced smell of volatile aldehydes, trimethylamine and ethylmercapatan, and had a satisfactory flavor, taste, and mouth feel.

Example B-3

Boiled-Dried Product

One hundred parts by weight of water were boiled in a large vessel, and in which were dissolved two parts by weight of an inhibitory agent in the form of a granule obtained by the method in Example A-12. After boiling the solution, 10 parts by weight of raw Japanese anchovies placed in a sieved basket was soaked therein to boil down. Then, the Japanese anchovy was drained off by putting the sieve basket out of the solution and dried in a usual manner to obtain the captioned product. The product, which the formation of volatile aldehydes and/or the decomposition of fatty acids are well inhibited and the freshness is also well retained, can be readily used to make a soup and has a satisfactory color tint, flavor, and taste.

Example B-4

Stripped Short Necked Clam

One hundred parts by weight of water were boiled in a large vessel and continued boiling after mixed with three parts by weight of a syrup containing α-oligoglucosyl α,α-trehaloses, obtained by the method in Example A-1. Into the boiling solution, 10 parts by weight of raw short necked clams were soaked with a sieve basket for boiling up, and then drained off by putting the sieve basket out of the solution and in a usual manner to obtain the captioned product boiled in water. The product, which the formation of volatile aldehydes and/or the decomposition of fatty acids were well inhibited, had a satisfactory color, gloss, flavor, and taste. The product can be arbitrarily used to make into "tsukudani" (a food boiled down in soy sauce), and used as a material for seafood curry and "gomoku-gohan" (a boiled rice mixed with fish and vegetables).

Example B-5

Boiled Octopus

Ten parts by weight of raw octopus were in a usual manner ground with salt using an inhibitory agent containing salt in a powder form obtained by the method in Example A-11, boiled down by placing in a large vessel with a boiling solution of 100 parts by weight of water which dissolved three parts by weight of an inhibitor agent in a tablet from obtained by the method in Example A-13. Thus, the captioned product was obtained. The product, which the formation of volatile aldehydes and/or the decomposition of fatty acids were well inhibited, had a satisfactory color, gloss, flavor, and taste. After cut into pieces with an appropriate size, the product can be arbitrarily used as a material for "sushi" (a vinegared fish and rice) and daily dishes such as fish and vegetables seasoned with vinegar, as well as Japanese hotchpotch.

Example B-6

Pacific Herring Soaked in Vinegar

A raw pacific herring fillet was in a usual manner slightly salted with an inhibitory agent in a powder form obtained by the method in Example A-11. After one-hour standing at ambient temperature, the salted product was soaked in a seasoning solution prepared by dissolving in 100 parts by weight of vinegar one part by weight of a tangle soup and five parts by weight of an α-oligoglucosyl α,α-trehalose syrup with hydrogenation treatment obtained by the method in Example A-8, and kept in the seasoning solution for five hours at ambient temperature to obtain the captioned product. The product, which the formation of volatile aldehydes and/or the decomposition of fatty acids were well inhibited, had a satisfactory color, gloss, flavor, and taste. After cut into pieces with an appropriate size, the product can be arbitrarily used as a material for "sushi" (a vinegared fish and rice) and daily dishes such as fish and vegetables seasoned with vinegar.

Example B-7

Yellowtail Cooked in Soy Sauce

One hundred parts by weight of sliced raw yellowtails were placed in a vessel, admixed with 10 parts by weight of soy sauce, five parts by weight of "mirin" (a sweet sake), 10 parts by weight of water, and 10 parts by weight of an α-oligoglucosyl α,α-trehalose syrup obtained by the method in Example A-1, and in a usual manner the resulting slices were cooked to obtain the captioned product. The product, which the formation of volatile aldehydes and/or the decomposition of fatty acids were well inhibited, had a satisfactory color, gloss, flavor, and taste.

Example B-8

Fish-Meat Paste Product

To 4,000 parts by weight of a thawed Alaska pollack paste was added 100 parts by weight of an aqueous solution prepared by dissolving in 300 parts by weight of ice water 80 parts by weight of an inhibitory agent in a granular form obtained by the method in Example A-12, 80 parts by weight of sodium glutamate, 200 parts by weight of potato starch, 12 parts by wight of sodium tripolyphosphate, 120 parts by weight of salt, and 10 parts by weight of maltitol. About 120 g aliquots of the resulting mixture were shaped and pasted unto plates and steamed for 30 min to increase their internal product temperature to about 80° C. Thereafter, the resulting products were cooled at ambient temperature, allowed to stand at 4° C. for 24 hours to obtain a fish meat paste product. The product, which the formation of volatile aldehydes and/or the decomposition of fatty acids were well inhibited, had a satisfactory flavor and taste, smooth and fine surface, and glossy shine.

Example B-9

Peanut Cream

To 55 parts by weight of an α-oligoglucosyl α,α-trehalose syrup obtained by the method in Example A-6 was admixed under heating conditions to homogeneity 12 parts by weight of a peanut butter, six parts by weight of a shortening, five parts by weight of an evaporated milk, 0.4 part by weight of an emulsifier, 0.2 part by weight of salt, 0.5 part by weight of a thickening agent, an adequate amount of a flavor, and 18 parts by weight of water. The resulting mixture was in a usual manner boiled down and bottled to obtain the captioned product.

The product, which the formation of volatile aldehydes and/or the decomposition of fatty acids were well inhibited, had a satisfactory color, gloss, flavor and taste.

Example B-10

Wheat Flour

To 100 parts by weight of a carefully selected wheat was added two parts by weight of an aqueous solution prepared by diluting a powder containing α-oligoglucosyl α,α-trehaloses obtained by the method in Example A-3 in water to give a saccharide concentration of about 40%. The resulting mixture was in a usual manner milled to obtain a wheat flour. The product contained about 0.3% of α-oligoglucosyl α,α-trehaloses to the weight of the product. The product, which the formation of volatile aldehydes and/or the decomposition of fatty acids are well inhibited, is a high-quality wheat flour with an improved storage stability. The product can be advantageously used in confectionery, bread, pasta, noodle, frozen pizza, and premixes. Since the wheat bran, produced as a by-product during the above milling processing, contained α-oligoglucosyl α,α-trehaloses, it well inhibits the formation of volatile aldehydes and/or the decomposition of fatty acids and has a satisfactory storage stability. Thus, the product can be arbitrarily used as a material for wheat germ oil and formula feed.

Example B-11

Open Top Bread made from Rice Four

To one hundred parts by weight of "RICE FLOUR™", a gluten-containing four for bread commercialized by Saito Seifun Co., Ltd, Niigata, Japan, were added 3.5 parts by weight, d.s.b., of "TREHA®", a high purity anhydrous crystalline trehalose with a trehalose content of at least 98% commercialized by Hayashibara Shoji, Inc., Okayama, Japan, five parts by weight, d.s.b., of the powder containing α-oligoglucosyl α,α-trehaloses in Example A-4, two parts by weight of "SELOGEN™" (sodium carboxymethyl cellulose), a derivative of cellulose produced by Dai-Ichi Kogyo Seiyaku Co., Ltd., Tokyo, Japan, three parts by weight of sucrose, two parts by weight of salt, 2.5 parts by weight of a sea yeast produced by SK Foods, Tokyo, Japan, 10 parts by weight of raw cream, five parts by weight of an evaporated milk, four parts by weight of a shortening, and 80 parts by weight of water. The resulting mixture was successively kneaded by using a mixer at a low mixing speed for six minutes and a middle mixing speed for three minutes at 23° C., suspending for a while, and then mixing with the mixer at a middle mixing speed for four minutes to obtain a dough. The resulting dough was fermented for 50 min as a floor time. The fermented dough was rounded after divided into lumps with a divisional specific volume of 3.5 (234 g×4 lumps), allowed to stand for 20 min as a bench time, placed in a container with a mold size of 3.5 cm to shape an open top bread, and placed in a final proof to ferment at 40° C. for 50 min under a relative humidity of 80%. After completion of the fermentation, the fermented dough was baked for 45 min in an oven adjusted to give the upper and lower fire temperatures of 230° C. and 200° C., respectively, to obtain the captioned product.

The open top bread obtained in this example was burnt brown with a satisfactory taste, increased volume, desired color tint, and preferable sliced surface texture. Since the product contained α,α-trehalose and α-oligoglucosyl α,α-trehaloses, it well inhibited the formation of volatile aldehydes and/or the decomposition of fatty acids. Even when stored at 5° C. for a week in a refrigerator, the product had a satisfactory storage stability without giving substantially no change in mouth feel and no dry up crispness due to hardening.

Example B-12

Salad Oil

One hundred parts by weight of soybeans selected carefully were pressed, and then sprayed and mixed as homogeneously as possible with four parts by weight of an aqueous solution prepared by dissolving a powder containing α-oligoglucosyl α,α-trehaloses obtained by the method in Example A-4 in water to give a saccharide concentration of about 25%. The resulting mixture was in a usual manner heated, treated with a solvent, i.e., n-hexan, to extract lipids. The extract was distilled in vacuo to remove solvent, degumming, desalted, decolored, deodorization, and subjected to purification steps including wintering to obtain the captioned product. A high quality salad oil can be easily produced because the formation of volatile aldehydes and/or the decomposition of fatty acids are well inhibited during the above steps of oil refining and heat treatment. The product with a high quality and storage stability can be arbitrarily used as oils and fats for "tenpura" (a Japanese deep-fat fried fish paste) and fried foods, as well as mayonnaises and dressings. Since the defatted soybeans, produced as a by-product during the above oil refining step, contained α-oligoglucosyl α,α-trehaloses, they well inhibit the formation of volatile aldehydes and/or the decomposition of fatty acids and have a satisfactory storage stability. Thus, the defatted soybeans can be arbitrarily used as a material for "tofu" (soybean curd), "abura-age" (a fried sliced tofu), soybean flour, "miso", soy sauce, and formula feed.

Example B-13

Dressing

Thirty-five parts by weight of vinegar, 15 parts by weight of a powder containing α-oligoglucosyl α,α-trehaloses obtained by the method in Example A-4, and 2.5 parts by weight of salt were mixed and further stirred while adding thereto a small amount of pepper. The mixture was further stirred while gradually adding thereto 50 parts by weight of salad oil to obtain the captioned product. The product, which the formation of volatile aldehydes and/or the decomposition of fatty acids are well inhibited and which has a satisfactory storage stability, can be arbitrarily used as a dressing to season salad, etc.

Example B-14

Mayonnaise

Seventeen parts by weight of egg yolk, 13 parts by weight of vinegar, three parts by weight of a powder containing α-oligoglucosyl α,α-trehaloses obtained by the method in Example A-2, one part by weight of sugar, one part by weight of spices, and 65 parts by weight of a salad oil were mixed by stirring with a mixer. The mixture was in a usual manner subjected to a homogenizer, filtered, and injected into a container to obtain the captioned product. The product is a highly valuable mayonnaise, which the formation of volatile aldehydes and/or the decomposition of fatty acids are well inhibited and which has a satisfactory color tint, taste, flavor, and storage stability.

Example B-15

Roasted Almond

One hundred parts by weight of almonds selected carefully were roasted in a usual manner and, while keeping the resultant at a relatively high temperature, sprayed and mixed as homogeneously as possible with two parts by weight of an aqueous solution prepared by dissolving a powder containing α-oligoglucosyl α,α-trehaloses obtained by the method in Example A-7 in water to give a saccharide concentration of about 20%. Thereafter, the resultant was sprinkled with a powdered salt to obtain the captioned product. The product, which the formation of volatile aldehydes and/or the decomposition of fatty acids are well inhibited and which has a satisfactory flavor, taste, and storage stability, can be arbitrarily used as a refreshment and a material for confectionery and bread.

Example B-16

Roasted Sliced-Almond

Commercially available sliced almonds, about 1 mm in thickness, were soaked in a syrup, containing α-oligoglucosyl α,α-trehaloses obtained by the method in Example A-6, at 70° C. for 10 min, drained, and roasted at 180° C. by using an electric oven to obtain the captioned product having satisfactory properties in any of color tint, texture, flavor, and taste. The product, which the formation of volatile aldehydes and/or the decomposition of fatty acids are well inhibited and which has a satisfactory storage stability, can be arbitrarily used intact as a refreshment and a material for confectionery and bread. Since the product is covered with a thin, glossy transparent layer of α-oligoglucosyl α,α-trehaloses, it has an attractive high quality.

Example B-17

Apple Fried in Vacuo

Apples were washed and fed to a slicer to obtain sliced apples, about 5 mm in thickness, which were then soaked for 15 min in an aqueous solution (60° C.) having a saccharide concentration of about 30% and a salt concentration of about 0.1%, which had been prepared by dissolving in water a powder containing α-oligoglucosyl α,α-trehaloses obtained by the method in Example A-9 and then adding salt thereunto, and then drained and freezed for storing at −20° C. The freezed product was in a usual manner fried in vacuo using edible oils and fats to obtain the captioned product having satisfactory properties in any of color tint, texture, flavor, and taste. The product, which the formation of volatile aldehydes and/or the decomposition of fatty acids are well inhibited and which has a satisfactory storage stability, can be arbitrarily used intact as a refreshment and a material for confectionery and bread.

Example B-18

Carrot Fried in Vacuo

Carrots were pealed and fed to a slicer to obtain sliced carrots, about 5 mm in thickness, which were then soaked for 20 min in an aqueous solution (60° C.) containing about 0.1% of salt and about 40% of a powder containing α-oligoglucosyl α,α-trehaloses obtained by the method in Example A-3, and then drained, subjected to branching for two minutes, and fried in vacuo in a usual manner using edible oils and fats to obtain the captioned product having satisfactory properties in any of color tint, texture, flavor, and taste. The product, which the formation of volatile aldehydes and/or the decomposition of fatty acids are well inhibited and which has a satisfactory storage stability, can be arbitrarily used intact as a refreshment, a material for confectionery and bread, and an additive for instant foods.

Example B-19

Chewing Gum

Three parts by weight of a gum base were melted by heating so as to be softened, and to which were added two parts by weight of "MABIT®, an anhydrous crystalline maltitol commercialized by Hayashibara Shoji, Inc., Okayama, Japan, two parts by weight of xylitol, three parts by weight of a powder containing α-oligoglucosyl α,α-trehaloses obtained by the method in Example A-1, and adequate amounts of a flavor and a color. The mixture was in a usual manner kneaded by a roll, shaped, and packaged to obtain the captioned product. The product, which the formation of volatile aldehydes from hardened oils and/or the decomposition of fatty acids in the oils are well inhibited, can be arbitrarily used as a chewing gum having a satisfactory texture, mouth feel, flavor and taste.

Example B-20

Caramel

One hundred and fifteen parts by weight of sugar, 140 parts by weight of condensed milk, and 170 parts by weight of a powder containing α-oligoglucosyl α,α-trehaloses obtained by the method in Example A-7 were heated to 35° C., and mixed by stirring. To the mixture were added 42 parts by weight of a hardened oil, 30 parts by weight of a butter, and three parts by weight of an emulsifier. The resulting mixture was emulsified by stirring and boiled down by heating up to 122° C., and then admixed with one part by weight of salt and a small amount of a flavor, fed to a cooling plate to extend to give a sheet, 8 mm in thickness, and cut into pieces of caramel by a cutter. The product is a high quality caramel, which the formation of volatile aldehydes and/or the decomposition of fatty acids are well inhibited and which has an improved storage stability.

Example B-21

Instant Noodle

Ninety-eight and a half parts by weight of a wheat flour (a strong flour), 1.5 parts by weight of an inhibitory agent obtained by the method in Example A-4, and 30 parts by weight of 0.5% kansui were mixed and in a usual manner kneaded and prepared into noodles, 0.9 mm in thickness. After the noodles were steamed for one minute and 15 seconds in a steamer, they were fried in a salad oil preheated to 145° C. for one minute and 20 seconds to obtain the captioned product.

After storage in a sealed container for one year at ambient temperature, the instant noodle was taken out of the container and to which was added boiled water. After 3-min standing, the cooked noodle was tasted and revealed to be delicious because it retained its original viscosity and elasticity just after its processing and the formation of volatile aldehydes and/or the decomposition of fatty acids were well inhibited.

Example B-22

Bacon

Twenty-two parts by weight of salt, 2.5 parts by weight of an inhibitory agent obtained by the method in Example A-4, two parts by weight of sugar, two parts by weight of sodium lactate, 2.0 parts by weight of sodium polyphosphate, 0.5 part by weight of L-ascorbic acid, 0.2 part sodium nitrite, and 68.8 parts by weight of water were mixed for dissolving into a pickle. To nine parts by weight of pork ribs was penetrated to homogeneity one part by weight of the pickle for sufficient period of time, and in a usual manner smoked to obtain the captioned product. Thereafter, the smoked bacon was allowed to stand overnight, packaged in vacuo, and stored at 10° C. The product, which the formation of volatile aldehydes and/or the decomposition of fatty acids were well inhibited, well retained its original flavor and taste even after a one week-standing. Since the product contained sodium lactate in addition to α-oligoglucosyl α,α-trehaloses, the bacterial contamination would be inhibited. Even when thawed after frozen storage, the product had a satisfactory flavor and taste because the protein denaturation and the syneresis of the product were satisfactorily inhibited.

Example B-23

Ice Cream

Eighteen parts by weight of a raw cream containing about 46% of oils and fats, seven parts by weight of a skim milk powder, 51 parts by weight of a whole milk, eight parts by weight of sugar, six parts by weight of a powder containing α-oligoglucosyl α,α-trehaloses obtained by the method in Example A-2, four parts by weight of "NYUKAOLIGO®", a powder containing lactosucrose, three parts by weight of a kneaded black sesame, one part by weight of pullulan, and two parts by weight of gum arabic were mixed to dissolve. The solution was sterilized by heating at 70 for 30 min, emulsified and dispersed by a homogenizer, instantly cooled to 3 to 4° C., aged overnight, and freezed by a freezer to obtain the captioned product. The product was a sesame-flavored ice cream, which the formation of volatile aldehydes and/or the decomposition of fatty acids were well inhibited and which had a satisfactory storage stability, mouth feel, and overrun. Since the product contains lactosucrose, it can be advantageously used as a health food with a bifid-bacteria-growth-promoting activity.

Example B-24

Barley Tea

One hundred parts by weight of a carefully selected barley were in a usual manner roasted, and to the resulting roasted product still retaining a relatively high temperature was sprayed and mixed to homogeneity with two part by weight of a 10% aqueous solution of α-oligoglucosyl α,α-trehaloses, prepared by diluting with water a syrup containing α-oligoglucosyl α,α-trehaloses obtained by the method in Example A-1. The resulting product was air-dried, injected into small bags and packaged to obtain the captioned product. The product is a barley tea with a satisfactory flavor and taste, which the formation of volatile aldehydes and/or the decomposition of fatty acids are well inhibited and which has an improved storage stability.

Example B-25

Green Tea Beverage

Three parts by weight of a green tea (a middle grade product) were exudated with 180 parts by weight of hot water. To the exudated solution were added and dissolved therein L-ascorbic acid, "αG RUTIN™", an α-glucosyl rutin commercialized by Hayashibara Shoji, Inc., Okayama, Japan, and a powder containing α-oligoglucosyl α,α-trehaloses obtained by the method in Example A-2 to give concentrations of 0.05% (w/v), 0.01% (w/v), and 0.7% (w/v), respectively. The solution was injected into a 500-ml transparent plastic bottle and sterilized to obtain the captioned product. The product, which the formation of volatile aldehydes and/or the decomposition of fatty acids and the browning are well inhibited, is a high quality green tea with a satisfactory color tint inherent to green tea, improved flavor, taste, and storage stability.

Example B-26

Royal Jelly Powder

To one part by weight of a royal jelly with a moisture content of 65% were added and dissolved therein three parts by weight of the powdery inhibitory agent in Example A-4, two parts by weight of "TREHA®", an anhydrous crystalline trehalose commercialized by Hayashibara Shoji, Inc., Okayama, Japan, and 0.5 part by weight of L-ascorbic acid 2-glucoside commercialized by Hayashibara Shoji, Inc., Okayama, Japan. The resulting mixture was in a usual manner dried in vacuo to obtain the captioned product. The product is a high quality royal jelly powder, which the formation of volatile aldehydes and/or the decomposition of fatty acids are well inhibited. The product with an improved water-solubility can be used intact or after optionally granulated or tabletted for use as health foods, as well as a material for other food products, cosmetics, quasi-drugs, and pharmaceuticals.

Example B-27

Processed Product of Wheat Germ

Seventy-eight parts by weight of a frozen raw wheat germ were thawed and admixed with 20 parts by weight of a powdery inhibitory agent prepared by the method in Example A-2, and two parts by weight of a previously prepared 5% aqueous solution of "PULLULAN PF-20™", a pullulan commercialized by Hayashibara Shoji, Inc., Okayama, Japan. The mixture was fed to an airtight extruder, heated, mixed, extruded to granule, and dried. The dried product was further roasted in a usual manner to obtain the captioned product. The product, which the formation of volatile aldehydes and/or the decomposition of fatty acids are well inhibited, has a nice-smelling, enriched flavor and taste, easily tastable property, and improved storage stability. Since the product is enriched in minerals such as selenium and zinc, as well as vitamins and edible fibers, it can be preferably used intact as a supplement for heath foods and a material for other food products.

Example B-28

Broccoli Powder

Commercially available broccoli was washed with water and finely sliced into pieces, about 3 mm in thickness. The pieces were placed in a stainless steel basket, and steamed for branching. Ninety parts by weight of the steamed product were admixed with 10 parts by weight of a powdery inhibitory agent, prepared by the method in Example A-3, followed by melting the agent to penetrate the α-oligoglucosyl α,α-trehaloses contained in the agent and air-drying the resultant at 55° C. for 14 hours. The dried broccoli was powdered by a pulverizer to obtain the captioned product. The product can be preferably used as a health food or a material thereof because the formation of volatile aldehydes and/or the decomposition of fatty acids are well inhibited and the color tint, flavor, taste, and nutrients, which are inherent to broccoli, will be stably retained for a relatively long period of time.

Example B-29

Powdered Tangle

To 100 parts by weight of a dried tangle were added 600 parts by weight of an aqueous solution containing 3% of a powdery inhibitory agent, prepared by the method in Example A-4, to totally absorb the aqueous solution. The resulting tangle was spread over stainless steel meshes and dried at 60° C. for 16 hours by using an air-drier to obtain a dried tangle. The dried tangle was powdered by a pulverizer to obtain the captioned product having an average particle size of about 11 µm. The product can be preferably used as a material for powdered seasonings and health-food supplements because the formation of volatile aldehydes and/or the decomposition of fatty acids are well inhibited and the flavor and taste will be well retained for a relatively long period of time without absorbing moisture.

Example B-30

Powdered *Lentinula edodes*

One hundred parts by weight of commercially available dried powdered *Lentinula edodes* were roughly crushed into tips, 3 to 4 mm in diameter. Twenty-four parts by weight of a solution, prepared by dissolving in 800 parts by weight of water 450 parts by weight of a powdery inhibitory agent obtained by the method in Example A-7, and 24 parts by weight of "PULLULAN PF-20™", a pullulan commercialized by Hayashibara Shoji, Inc., Okayama, Japan, were added to the tips to be totally absorbed therein. The resulting tips were spread over a tray and dried by using an air-dryer at 60° C. for 18 hours. The product obtained by the above method was powdered by a pulverizer to obtain the captioned product with a moisture content of about 6%. The product, which the formation of volatile aldehydes and/or the decomposition of fatty acids are well inhibited, can be preferably used as a material for powdered seasonings and health-food supplements because it will well retain the original flavor and taste without absorbing moisture even when stored for a relatively long period of time.

Example B-31

Powdered Dried Strip

A powdery hydrogenated inhibitory agent prepared by the method in Example A-9 was dissolved in water to give a concentration of 35%, d.s.b. In the resulting aqueous solution was soaked a fresh Japan tuna, which had been cut into fillets, thoroughly boiled and treated in a usual manner to obtain a dried strip, followed by powdering the dried strip by a pulverizer to obtain the captioned product with a moisture content of about 5%. The product, which the formation of volatile aldehydes and/or the decomposition of fatty acids are well inhibited, can be preferably used as a material for powdered seasonings and health-food supplements because it will well retain the original flavor and taste without absorbing moisture even when stored for a relatively long period of time.

Example B-32

Process Cheese

One hundred and fifty parts by weight of a crushed commercialized Gouda cheese, 7.5 parts by weight of water, three parts by weight of the powdery inhibitory agent in Example A-4, and 4.5 parts by weight of sodium citrate as an emulsifier were placed in an emulsifying vessel and allowed to melt while stirring and indirectly heating the contents with a steam jacket to give a temperature of 80° C. for 10 min. After suspending the heating, the mixture was further stirred, deairated in vacuo, injected into a vessel while keeping the contents at 50° C. or over, and packaged to obtain the captioned product. The product, which the formation of volatile aldehydes and/or the decomposition of fatty acids are well inhibited, is a high quality process cheese.

Example B-33

Coating Material for Fried Foods

To 90 parts by weight of a soft flour, five parts by weight of corn starch, and 1.5 parts by weight of a baking powder was added 3.53 parts by weight of the hydrogenated powder of α-oligoglucosyl α,α-trehaloses prepared in Example A-9 to obtain the captioned product, i.e., a coating for tenpura. When used to fry foods in a usual manner, the product containing non-reducing saccharides less induced browning. The product, which the formation of volatile aldehydes and/or the decomposition of fatty acids are well inhibited, can be preferably used to fry foods.

Example B-34

Liqueur

Ninety-five parts by weight of a commercially available liqueur was admixed with five parts by weight of a syrup containing α-oligoglucosyl α,α-trehaloses prepared by the method in Example A-1. The product is a liqueur, which the decomposition of fatty acids are inhibited. When used in seasonings for cooking or processing fish eggs and fishery products such as fish, the product will inhibit the decomposition of fatty acids contained therein and also inhibit the formation of volatile aldehydes induced by heating, etc., and this facilitates to produce cooked or processed foods with a satisfactory flavor and taste.

Example B-35

Chocolate Moose

Seventy parts by weight of chocolate were cut, melted by heating in a water bath, kneaded after the addition of 13 parts by weight of butter, and gradually admixed well with 30 parts by weight of egg yolk while heating in the water bath, followed by suspending the heating when the mixture became sticky. A paste with chocolate was prepared by adding to the above product a mixture, which had been prepared by swelling six parts by weight of a gelatin powder with a small amount of water, melting the gelatin by heating in a water bath, and admixing the resulting mixture with a small amount of rum. Then, the resulting paste was rigidly formed by the addition of 60 parts by weight of egg white, 12 parts by weight of sugar, and six parts by weight of the saccharide powder containing α-oligoglucosyl α,α-trehaloses in Example A-2. The mixture was placed in a container and solidified by cooling to obtain the captioned product.

Since the product containing α-oligoglucosyl α,α-trehaloses, it inhibits both the decomposition of fatty acids contained in chocolate, butter and eggs and the formation of volatile aldehydes. Thus, the product is a high quality chocolate moose which can retain a satisfactory flavor and taste for a relatively long period of time.

Example B-36

Bath Salt

Five parts by weight of the powdery inhibitory agent in Example A-4, 40 parts by weight of sodium sulfate, 31 parts by weight of sodium bicarbonate, 20 parts by weight of sodium carbonate, and four parts by weight of a flavor were mixed and pulverized by a pin-mill to obtain the captioned product. The product well inhibits the formation of volatile aldehydes from sweat, dirt, dandruff, and sebum, and it can be advantageously prevent the generation of body odor and prevent skin stimulation and itch.

Example B-37

Cosmetic Milky Lotion

A half part by weight of polyoxyethylene behenyl ether, 1.0 part by weight of polyoxyethylene sorbitol tetraoleate, 1.0 part by weight of oil-soluble glycerol monostearate, 0.5 part by weight of behenyl alcohol, 1.0 part by weight of avocado oil, 0.1 part by weight of linoleic acid, and adequate amounts of vitamin E and a preservative were melted by heating in a usual manner. To the mixture were added 5.0 parts by weight of 1,3-butylene glycol, 3.5 parts by weight of sodium L-lactate, 3.0 parts by weight of a syrup containing α-oligoglucosyl α,α-trehaloses obtained by the method in Example A-6, 0.1 part by weight of carboxyvinyl polymer, and 80.3 parts by weight of refined water and emulsified with a homogenizer, and further mixed with an adequate amount of a flavor to obtain a milky lotion.

The product is a skin-whitening agent, which the formation of volatile aldehydes and/or the decomposition of fatty acids and which stably retains its high quality. The product well inhibits the formation of volatile aldehydes from sweat, dirt, dandruff, and sebum, as well as the formation of fatty acids; and prevents the generation of body odor and prevent skin stimulation and itch. The product can be advantageously used in agents for treatment and prevention of chromatosis such as freckle, spot, and sunburn. Since the product is incorporated with non-reducing saccharides, it is a high-quality cosmetic milky lotion whose browning during storage will be well inhibited.

Example B-38

Fat Emulsifier for Injection

Ten parts by weight of soybean salad oil, 1.0 part by weight of soybean lecithin, 90 parts by weight of water, and 10 parts by weight of a pyrogen-free α-maltotetraosyl α,α-trehaloses enriched powder obtained by the method in Example A-5 were mixed and stirred by a mixer for 10 min to obtain a coarse emulsifier. Then the resulting emulsifier was homogenized by a pressure injection-type emulsifier produced by Manton-Gaulin Company, MA, USA, under the stream of nitrogen gas at a pressure of 600 kg/cm$^2$ to obtain a minute particle emulsifier with a mean average size of 0.2μ or lower. The emulsifier thus obtained was in a usual manner sterilized with a membrane filter and distributed into vials for injection, followed by sealing the vials and then sterilizing them by heating to prepare the captioned product.

The product is a fat emulsifier for intravenous injection, which well inhibits the formation of volatile aldehydes and/or the decomposition of fatty acids and which stably keeps its high quality. Also the product can be preferably used as an orally- or intubationally-administrable fluid food for supplementing energy.

INDUSTRIAL APPLICABILITY

As described above, the present invention provides a method for inhibiting the formation of volatile aldehydes per se from either fatty acids or products containing the same and/or the decomposition of such fatty acids; a composition obtainable by the method; an agent comprising α-oligoglucosyl α,α-trehalose(s) as an effective ingredient, which inhibits the formation of volatile aldehydes and/or the decomposition of fatty acids; and uses thereof. In practicing the present invention, since α-oligoglucosyl α,α-trehaloses are non-reducing saccharides and stable saccharides, the nutritious ingredients and umami ingredients (or delicious ingredients) such as vitamins, amino acids, and peptides, which are contained in fatty acids or products containing the same, for example, food products, cosmetics, pharmaceuticals, and their materials and intermediates, can be stored and/or processed without deteriorating them, while characteristically, stably retaining the desired high quality of the final compositions. The establishment of the present invention will provide a novel means for storing and/or processing fatty acids and/or products containing the same, and provide products such as high quality and stable food products, cosmetics, pharmaceuticals, and their materials and intermediates. Accordingly, the present invention will extensively influence, particularly, on the fields of agricultural/fishery products, food products, health foods, cosmetics, and pharmaceuticals; and will give an unfathomable industrially significant influence on the fields.

The invention claimed is:

1. A method for inhibiting the heat decomposition of fatty acids in nuts or seeds containing fatty acids, said method comprising:
incorporating α-maltosyl α,α-trehalose in the nuts or seeds in an amount of at least about 50%, but below about 98%, on a dry solid basis, to the weight of the fatty acids in the nuts or seeds, before, during or after a heating processing, without imparting an over-sweetness to a resulting processed nuts or seeds as compared to those prepared with α,α-trehalose, thereby inhibiting the heat decomposition of fatty acids in the nuts and seeds.

* * * * *